United States Patent [19]
Emalfarb et al.

[11] Patent Number: 6,015,707
[45] Date of Patent: Jan. 18, 2000

[54] TREATING CELLULOSIC MATERIALS WITH CELLULASES FROM CHRYSOSPORIUM

[75] Inventors: Mark Aaron Emalfarb, Jupiter, Fla.; Arie Ben-Bassat, Wilmington, Del.; Arkady Panteleimonovich Sinitsyn, Moscow, Russian Federation

[73] Assignee: Mark A. Emalfarb, Jupiter, Fla.

[21] Appl. No.: 09/106,026

[22] Filed: Jun. 29, 1998

Related U.S. Application Data

[62] Division of application No. 08/731,170, Oct. 10, 1996, Pat. No. 5,811,381.

[51] Int. Cl.[7] .............................. D06M 16/00; D21C 1/00; D21C 3/00; C09B 67/00
[52] U.S. Cl. .......................... 435/263; 435/277; 435/278; 8/401
[58] Field of Search ..................................... 435/263, 277, 435/278; 8/401

[56] References Cited

U.S. PATENT DOCUMENTS 3,966,543  6/1976  Cayle et al. .............................. 162/158
4,610,800  9/1986  Durham et al. .......................... 510/195

OTHER PUBLICATIONS

Reese et al., "Beta–D–1,3 glucanases in fungi," Canadian Journal of Microbiology (1959), vol. 5, pp. 173–185.

*Primary Examiner*—Robert A. Wax
*Attorney, Agent, or Firm*—Morgan & Finnegan, LLP

[57] ABSTRACT

The subject invention relates to novel compositions of neutral and/or alkaline cellulase and methods for obtaining neutral and/or alkaline cellulase compositions from Chrysosporium cultures, in particular *Chrysosporium lucknowense*. This invention also provides mutants and methods of generating mutants of Chrysosporium capable of producing neutral and/or alkaline cellulase. This invention also relates to the genes encoding the enzymes comprising the neutral and/or alkaline cellulase composition. In addition, this invention provides methods of culturing Chrysosporium to produce neutral and/or alkaline cellulases. The neutral and/or alkaline cellulase compositions of the subject invention can be used in a variety of processes including stone washing of clothing, detergent processes, deinking and biobleaching of paper & pulp and treatment of waste streams.

50 Claims, No Drawings

TREATING CELLULOSIC MATERIALS WITH CELLULASES FROM CHRYSOSPORIUM

CROSS-REFERENCE TO RELATED APPLICATION

This is a divisional of co-pending application Ser. No. 08/731,170 filed Oct. 10, 1996, now U.S. Pat. No. 5,811,381.

FIELD OF THE INVENTION

This invention relates to neutral and/or alkaline cellulases and novel methods for producing the same. More specifically this invention relates to cellulases produced by fungi of the genus Chrysosporium, and particular strains of *Chrysosporium lucknowense*. This invention also relates to industrial uses for these neutral or alkaline cellulases and compositions comprising the same.

BACKGROUND OF THE INVENTION

Clothing made from cellulosic fabrics such as cotton, linen, hemp, ramie, cupro, lyocell, newcell, rayon, polynosics, are very popular. Of particular interest are clothing items such as jeans made from indigo-dyed denim fabrics made of cotton or cotton blends. Such clothing items are typically sewn from sized and cut cloth and tend to be stiff due to the presence of sizing compositions. In other cases the fibers or rolls of fabric are treated with enzymes prior to sewing the final garment. After a period of wear, the clothing items can develop a certain degree of softness, an overall reduction of shade as well as localized areas of color variation. Additionally, after repeated washing the garment continues to provide a more comfortable fit, a softer feel and a worn appearance. In recent years such comfort, feel and appearance have become increasingly popular.

The most widespread methods for producing this comfort, feel and look involve washing of clothing items with cellulases in large washing machines with pumice stones or other abrasives. The pumice helps soften the fabric and helps to provide the faded surface similar to that produced by the extended wear of the fabric. However, the use of pumice has some disadvantages. For example, the pumice must be manually removed from processed clothing items because it tends to accumulate in pockets, on interior surfaces, in creases, and in folds. Also, the pumice stones can cause overload damage to electric motors of stone washing machines, and clog machine drainage passages and drain lines. These processing and equipment problems can add significantly to the cost of doing business and to the purchase price of the goods.

In view of the problems of using pumice, alternative methods to using pumice or other abrasives in the stone washing process have been sought. One alternative involves the use of enzyme treatments which break down the cellulose in fabrics (Geller U.S. Pat. No. 4,951,366; Olson U.S. Pat. Nos. 4,832,864, 4,912,056, Olson et al. U.S. Pat. Nos. 5,006,126, 5,122,159 and 5,213,581, Christner et al. U.S. Pat. No. 4,943,530, Boegh et al. U.S. Pat. No. 4,738,682). Methods for treating cellulose containing fabrics with hydrolytic enzymes, such as cellulases, are known in the art to improve the softness or feel of such fabrics (Novo Brochure Cellulase SP 227; Novo Brochure Celluzyme; Murata U.S. Pat. No. 4,443,355; Parslow U.S. Pat. No. 4,661,289; Tai U.S. Pat. No. 4,479,881; Barbesgaard U.S. Pat. No. 4,435,307; Browning UK Patent No. 1,368,599).

Cellulases are known in the art as enzyme systems that hydrolyze cellulose ($\beta$-1,4-glucan linkages), thereby resulting in the formation of glucose, cellobiose, cellooligosaccharides, and the like. Cellulase compositions are comprised of several different enzyme components, including those identified as exocellobiohydrolases, endoglucanases, and $\beta$-glucosidases. Moreover, these classes of enzymes can be further separated into individual isoenzymes.

The complete cellulase system is required to efficiently convert crystalline cellulose to glucose. Generally, if total hydrolysis of a cellulose substrate is needed, the cellulase mixture should contain $\beta$-glucosidases and cellobiohydrolases, as well as endoglucanases. Endoglucanases catalyze random hydrolysis of $\beta$-1,4-glycosidic bonds between glucose units of cellulose polymers. Such components hydrolyze soluble cellulose derivatives such as carboxymethylcellulose, thereby reducing the viscosity of such solutions. Such enzyme components act on internal regions of the polymer, resulting in a rapid decrease in average polymer chain length together with a slow increase in the number of reducing ends. The rapid decrease in average chain length of the cellulose polymer is evidenced by the decrease in viscosity of a cellulose solution.

The substrate specificity and mode of action of the different cellulases varies among strains of organisms that produce cellulases. For example, the currently accepted mechanism of cellulase action in cellulase from the fungus *Trichoderma reesei* is that endoglucanase activity first break internal $\beta$-1,4-glucosidic bonds in regions of low crystallinity of the cellulose (Ruohnen L., et al. In: "Proceedings of the Second Tricel Symposium on *Trichoderma Reesei* Cellulases and Other Hydrolases", (ed. by P. Sudminen and T. Reinkainen.,) Foundation for Biotechnology and Industrial Fermentation Research 8; (1993):87–96) The cellobiohydrolase activity binds preferentially to the crystalline regions of the non-reducing end of the cellulose to release cellobiose as the primary product. $\beta$-Glucosidase or cellbiase activities then act on cellooligosaccharides, e.g., cellobiose, to give glucose as the sole product.

Cellulases are produced in fungi, bacteria, and other microbes. Fungi typically produce a complete cellulase system capable of degrading crystalline forms of cellulose. For example, *Trichoderma reesei* produces and secreates all of the enzyme activities needed for efficient breakdown of crystalline cellulose, namely endo-1,4-$\beta$-D-glucanases, cellobiohydrolases (exo-1,4-$\beta$-D-glucanases), and 1,4-$\beta$-D-glucanases, or $\beta$-glucosidases. Fungal cellulases have an added advantage in that cellulases in fungi can readily be produced in large quantities via fermentation procedures.

Cellulases, or the components thereof, are known in the art to be useful in a variety of industrial textile applications in addition to the stone washing process. For example, cellulases are used in detergent compositions, either for the purpose of enhancing the cleaning ability of the composition or as a softening agent. When so used, the cellulase will degrade a portion of the cellulosic material, e.g., cotton fabric, in the wash, which facilitates the cleaning and/or softening of the fabric. The endoglucanase components of fungal cellulases have also been used for the purposes of enhancing the cleaning ability of detergent compositions, for use as a softening agent, and for use in improving the feel of cotton fabrics, and the like. However, there is a problem with using the cellulase derived from Trichoderma spp. and especially *Trichoderma longibrachiatum* in detergent compositions. Generally, such components have their highest activity at acid pHs whereas most laundry detergent compositions are formulated for use at neutral or alkaline conditions.

Other textile applications in which cellulases have been used include softening (Browning, UK Patent No. 1,368, 599, Parslow, U.S. Pat. No. 4,661,289, Tai U.S. Pat. No. 4,479,881 and Barbesgaard, U.S. Pat. No. 4,435,307), defibrillation (Gintis, D. Mead, E. J., *Textile Research Journal*, 29, 1959; Cooke, W. D., *Journal Of The Textile Research Institute*, 74, 3, 1983; Boegh, European Patent Application No. 0 220 016). Cellulases have also been used in combination with a polymeric agent in a process for providing localized variation in the color density of fibers. (WO/94/19528 and WP/94/1529).

Cellulases are classified in the garment and textile industry according to their pH range of operation. Acid cellulases typically have their peak activity at pH values of about 4.0 to 5.5 and less, neutral cellulases at about pH 5.5 to 7.5, and alkaline cellulases at about pH 7.5 to 11.0. Some enzyme compositions may have broader ranges of operation. For example, the neutral/alkaline cellulases may operate at acid, neutral and alkaline pH's at between about 40° C. to 60° C.

Acid, neutral and alkaline cellulases are typically used in the "stone wash" treatment of denim jeans, with or without surfactants, buffers, detergents, anti-redeposition agents, softening agents, pumice stones or other abrasives, bleaching agents, such as optical bleaching agents, enzymes, or other means.

If the cellulase composition is not formulated and/or pre-buffered then for acid cellulases, the pH is typically adjusted to between pH 4.5–5.5, with for example, a sodium citrate and citric acid buffer, and for neutral or alkaline cellulases between 5.5–7.5 with, for example, a monosodium and disodium phosphate buffer. Neutral and alkaline cellulases are typically used as additives to laundry detergents where the pH of operation may range from about pH 7.0 to 11.5. In stone wash applications typical acid cellulases generally provide greater backstaining or redeposition of the indigo dye and greater strength loss of the fabric while the typical neutral and alkaline cellulases generally provide less abrasion, lower backstaining or redeposition and less strength loss of the fabric.

The neutral/alkaline cellulases are the most preferred type of cellulases for the stonewash industry because they cause lower levels of backstaining or redeposition and lower strength loss than acid cellulases (ie, from Trichoderma spp.). Furthermore, neutral/alkaline cellulases, unlike their acid counterparts, operate at a much wider pH range and are able to maintain better relative wash performance within a wider pH range (pH 5.0–pH 8.0) in the stone washing industry. Therefore, neutral/alkaline cellulases provide several advantages. First, the incoming feed water in wet processing facilities is typically within this pH range lessening the need for as precise pH control as compared to acid cellulases. This makes the stonewashing process more tolerant to operator pH error or neglect leaving the overall procedure more forgiving than procedures using acid cellulases. Secondly, it is known that denim fabrics are alkaline in nature owing to the fact that the dyeing process utilities caustic soda. Simply washing denim releases this caustic into the wash water and the pH of the wash water generally rises. The alkalinity may overcome the bath buffers, but the effect of increased pH is less severe on neutral/alkaline cellulases compared to acid cellulases because neutral/alkaline cellulases operate not only at higher pH, but also over a wider pH range.

The wide spectrum of industrial uses for cellulases or the components of cellulases, especially alkaline and/or neutral cellulases, establishes a clear need for cellulases that are operative at neutral and/or alkaline pH. The present invention provides a procedure for producing neutral/alkaline cellulases having enzymatic activity at neutral and/or alkaline pH's and compositions comprising the same.

SUMMARY OF THE INVENTION

This invention relates, in general, to neutral and/or alkaline cellulases and novel methods for producing the same. More specifically, the subject invention provides a method for producing cellulase compositions from fungi of the genus Chrysosporium, and particular *Chrysosporium lucknowense*, wherein the cellulase compositions have enzymatic activity at neutral and/or alkaline pH's. Industrial applications for the cellulase composition are also provided.

One embodiment of this invention relates to isolated and purified cultures of wild type and mutant fungi of the genus Chrysosporium capable of producing neutral and/or alkaline cellulase compositions, in particular to the strain *Chrysosporium lucknowense*—GARG 27K and mutants thereof.

Yet another embodiment of this invention provides culturing conditions for producing neutral or alkaline cellulases from fungi of the genus Chrysosporium.

In a further embodiment, this invention provides methods to producing a neutral and/or alkaline cellulase composition through recombinant technology from fungi of the genus Chrysosporium.

In yet a further embodiment of this invention methods for generating and culturing mutant strains of the fungi Chrysosporium capable of producing neutral and/or alkaline cellulase are provided.

Another embodiment of this invention relates to the nucleic acid sequences encoding the enzymes of the cellulases compositions produced by Chrysosporium or genetically modified strains of Chrysosporium.

Another embodiment relates to the purified and isolated enzymes of the cellulase compositions produced by Chrysosporium or genetically modified strains of Chrysosporium.

In yet another embodiment of this invention methods of use are provided for alkaline and/or neutral cellulases produced by Chrysosporium in textile applications, such as softening, bleaching and stone washing procedures, garment dyeing applications, defibrillation, or biopolishing.

Another embodiment of this invention relates to detergent compositions comprising Chrysosporium cellulase in detergent preparations.

Another embodiment of this invention is to provide methods of use for the cellulase compositions in the saccharification of lignocellulose biomass from agriculture, forest products, municipal solid waste, and other sources.

Yet other embodiments of this invention involve the use of the cellulase compositions for production of fuels and other chemicals for the biobleaching of wood pulp, and for de-inking of recycled print paper.

DETAILED DISCLOSURE OF THE INVENTION

As utilized herein, reference to a "neutral-alkaline cellulose" refers to a cellulase composition which retains significant enzymatic activity at pH values of about 5.5 and above. In a preferred embodiment, the neutral and/or alkaline cellulase compositions of the subject invention have peak enzymatic activity between about pH 5.5 to about 7.5 at 40° C. to about 60° C. In the event that the peak enzymatic activity is at a pH of less than about 5.5, the neutral-alkaline cellulase composition will have at least about 50% of the optimal enzymatic activity at about pH 6.0 to about 7.0 at about 40° C. to about 60° C. By way of example such activities may be measured by RBBCMCase, CMCase, endoviscometric or filter paper activity (FPA). Thus, the cellulase compositions of the subject invention will have useful enzymatic activity at pHs greater than 5.5 such that the enzyme composition can be used in stone wash, detergent, de-inking or other applications where neutral and/or alkaline cellulase activity is needed.

The subject invention relates to compositions of cellulases having high activity at neutral or alkaline pH's and to unique methods for producing said neutral and alkaline cellulase compositions. The neutral/alkaline cellulase compositions of this invention may be obtained from any species of Chrysosporium. In a particularly preferred embodiment, the cellulase compositions of the present invention are isolated from *Chrysosporium lucknowense* Garg 27K (designated isolate C1) deposited under the Budapest Treaty with the International Depository at the All-Russian Collection of Microorganisms of the Russian Academy of Sciences, Bakhrushina St. 8: Moscow, Russia 113184, on Aug. 29, 1996, and assigned accession number VKM F-3500D. The cellulase compositions of the subject invention are highly advantageous because they possess enzymatic activity at neutral and/or alkaline pH thereby providing beneficial performance characteristics in industrial applications.

The cellulase compositions prepared from fungal strains of the subject invention exhibit activity at between about pH 5.0 to about 12.0 at between about 40° to 60° C. as determined by a CMCase, RBBCMCase or endoviscometric assays. In a preferred embodiment for a stone wash procedure, the cellulase composition may have optimal activity at between about pH 5.5 to 7.0 at about 40° C. to about 60° C. Good performance activity at neutral and alkaline pH (i.e., 6.0, 7.0 & 8.0) has been demonstrated for the neutral and/or alkaline cellulases of the instant invention in Stonewash application trials and at pH 10.0 and above for detergent application trials.

The fermentation procedures for culturing cellulolytic microorganisms for production of cellulase are known in the art. For example, cellulase systems can be produced either by solid or submerged culture, including solid state, batch, fed-batch, and continuous-flow processes. The collection and purification of the cellulase systems from the fermentation broth can also be effected by procedures known in the art. The cellulase composition is readily isolated from the fungal culture by, for example, centrifugation or filtration steps and concentration of the filtrate via membrane or hollow fibers ultrafiltration equipment.

The fungal strain Chrysosporium used to produce the cellulase compositions of the subject invention can be cultured according to standard methods and conditions known in the art. In a preferred embodiment, the cellulase composition of the subject invention is obtained from the C1 strain. The C1 Chrysosporium strain may be grown in a medium containing inorganic salts, organic nitrogen sources, such as peptones, defatted cotton seed flour, corn steep liquor, or yeast extract and carbon source. Examples of carbon source include, but is not limited to, glucose, lactose, sucrose, cellulose or other carbohydrates. More preferably, the fungal strain is grown in media containing both lactose and peptone or lactose and yeast extract. By way of example the fermentation media can compose lactose at about 0.3% to about 1.0%, preferably about 0.5% to about 0.6%, peptone at about 0.3% to about 1.0%, preferably about 0.5% to about 0.6%. Other nitrogen sources and carbohydrate sources known in the art may be used in the fungal growth media including, but not limited to, sweet beet pulp, barley malt, wheat bran, and others known in the art. By way of example sweet beet pulp concentrate may be used in a range of about 15 to about 30 grams/liter (g/L), preferably about 20 to about 25 g/L; barley malt may be used in a range about 10 g/L to about 20 g/L, preferably about 14 g/L or about 16 g/L, wheat bean may be used in a range about 3 g/L to about 8 g/L, preferably about 5 g/L to about 6 g/L. In one embodiment, the C1 strain is cultured in rotated shake flasks in saline medium containing sweet beet pulp, barley malt, and wheat bran. Cellulase compositions may be isolated from fungi cultured about 3 to 7 days in a growth medium by centrifugation and ultrafiltration concentration of the cell culture medium.

Alternatively the Chrysosporium cultures can be cultured on a large scale for commercial use, by using conventional fermentation techniques. In this context fermentation is used broadly to refer to any controlled fungal culturing conditions. Prior to large scale growth an inoculum of said growth culture is generally cultured. The inoculum media may contain conventional ingredients including, but not limited to, carbon sources, organic nitrogen sources, and inorganic salts. Carbon sources may include, but are not limited to, glucose, lactose, glycerol, and/or cellulose at concentrations in the range of about 0.5 to 200 g/L, more preferably in the range of about 5 to 50 g/L. Organic nitrogen sources may include, but are not limited to, yeast extract, peptone, or defatted cotton seed flour at concentrations in the range of about 0.5 to 30 g/L, more preferably in the range of 5 to 15 g/L. Inorganic salts may include, but are not limited to, potassium phosphate, for example at about 0.01 to about 10 g/L, magnesium sulfate, for example at about 0.01 to 3.0 g/L, ferrous sulfate, for example at about 0.001 to 10 mg/L.

An inoculum or starter culture may be used to initiate the Chrysosporium culture for a fermenter by methods known in the art. The media used for fermentation may comprise conventional ingredients for culturing fungi, including but not limited to, cellulose, organic nitrogen sources, magnesium chloride and calcium chloride. Examples of organic nitrogen sources include, but are not limited to, peptone or defatted cotton seed flour, such as PHARMAMEDIA.

By way of example, the media may comprise about 5 g/l to about 20 g/L of peptone or defatted cotton seed flour, about 10 g/L to about 30 g/L of cellulose, about 0.03 g/L to about 0.06 g/L of magnesium sulfate heptahydrate and about 0.4 g/L to about 0.8 g/L of calcium chloride dihyrate.

One of skill in the art will appreciate that during fermentation the temperature, oxygenation, pH, and nutrient levels of fermentation mixture should be maintained. By way of example, dissolved oxygen levels should be maintained at about 10 to 60% of air saturation, preferably at about 20 to 40% of air saturation. The pH should be maintained between about 5 and 8, preferably between about 6.5 and 7.5, most preferably between 6.9 and 7.1 and the temperature may be maintained at between about 25° C. to about 40° C., preferably at about 28° C. to 35° C. The feed solution may comprise ingredients similar to the fermentation media but at higher concentrations to minimize dilution when added to the fermentation media.

The cellulase compositions produced according to the methods of the subject invention are useful for a variety of other applications for which cellulase activity, in particular neutral and/or alkaline cellulase activity, is needed. In one embodiment of this invention, the neutral and/or alkaline cellulase compositions can be used in stone washing procedures for denim jeans. By way of example, the most preferred pH range of stone wash applications is between about 5.5 to 7.5, most preferably at about pH 6 to about 7. The neutral and/or alkaline cellulase composition obtained from Chrysosporium isolates advantageously have significant enzymatic activity at or above neutral or alkaline pH. Stone wash procedures conducted with neutral and/or alkaline cellulase run at neutral and/or alkaline pH's are particularly advantageous compared to traditional procedures using acid cellulases (e.g., those from *Trichoderma reesei*) because of lower levels of backstaining on the garments, less strength loss to the garments and the alkalinity of the water that is present naturally during this process. These stone washing procedures result in jeans with highly desirable feel and appearance. By way of example, 0.02 to 10 g of cellulase preparation 47.0528 described herein, may be used per 135 g of denim. One of skill in the art will know how to regulate the amount or concentration of the cellulase composition produced by this invention based on such factors as the activity of the cellulose, and the wash conditions, including but not limited to temperature and pH.

In yet another embodiment of this invention, the cellulase compositions of this invention can be used to reduce or eliminate the harshness associated with fabrics made from cellulose by addition to detergent compositions. By way of example, the preferred range for detergent compositions is between about pH 8 to about 12, most preferably pH 10 to about 11. The cellulase compositions of the subject invention can be used in detergent compositions at neutral and or alkaline pH. Detergent ingredients contemplated for use with the cellulase composition of the subject invention include any detergent ingredient known in the art. Examples of such ingredients include, but are not limited to, detergents, buffers, surfactants, bleaching agents, softeners, solvents, solid forming agents, abrasives, alkalis, inorganic electrolytes, cellulase activators, antioxidants, builders, silicates, preservatives, and stabilizers, and are known in the art. The detergent compositions of this invention preferably employ a surface active agent, i.e., surfactant, including anionic, non-ionic, and ampholytic surfactants well known for their use in detergent compositions. In addition to the cellulose components and the surface active agent, the detergent compositions of this invention can additionally contain one or more of the following components; the enzymes amylases, cellulases, proteinase, and lipases; cationic surfactants and long-chain fatty acids; builders; antiredeposition agents; bleaching agents; bluing agents and fluorescent dyes; caking inhibitors; masking agents for factors inhibiting the cellulase activity; cellulase activators; antioxidants; and solubilizers. In addition, perfumes, preservatives, dyes, and the like can be used, if desired, with the detergent compositions of this invention. Examples of detergent compositions employing cellulases are exemplified in U.S. Pat. Nos. 4,435,307; 4,443,355; 4,661,289; 4,479,881; 5,120,463, which are herein incorporated by reference.

When a detergent base used in the present invention is in the form of a powder, it may be one which is prepared by any known preparation method including a spray-drying method and/or a granulation method. The granulation method are the most preferred because of the non-dusting nature of granules compared to spray dry products. The detergent base obtained by the spray-drying method is hollow granules which are obtained by spraying an aqueous slurry of heat-resistant ingredients, such as surface active agents and builders, into a hot space. The granules have a size of from about 50 to about 2000 micrometers. After the spray-drying, perfumes, enzymes, bleaching agents, and/or inorganic alkaline builders may be added. With a highly dense, granular detergent base obtained by such as the spray-drying-granulation method, various ingredients may also be added after the preparation of the base. When the detergent base is a liquid, it may be either a homogenous solution or an inhomogeneous solution.

The cellulase compositions of this invention preferably exhibit high levels of activity at alkaline or neutral pH's, but also may exhibit enzymatic activity at acidic pH's. Therefore, the detergent compositions comprising the cellulases of the present invention can be used in a broad pH range of from acidic to alkaline pH.

Other textile applications in which these cellulase compositions may be used include, but are not limited to, Garment Dyeing applications including but not limited to Enzymatic Mercerizing of viscose, Bio-Polishing applications, Enzymatic Surface Polishing; Biowash (washing or washing down treatment of textile materials), Enzymatic Microfibrillation, Enzymatic "cottonization" of linen, ramie and hemp; and treatment of Lyocel or Newcell (e.g.; "TENCEL" from Courtauld's), Cupro and other cellulosic fibers or garments, dye removal from dyed cellulosic substrates such as dyed cotton (Leisola & Linko (1976) *Analytical Biochemistry*, v. 70, p. 592. Determination Of The Solubilizing Activity Of A Cellulase Complex With Dyed Substrates; Blum & Stahl—Enzymic Degradation Of Cellulose Fibers; Reports of the Shizuoka Prefectural Hamamatsu Textile Industrial Research Institute No. 24 (1985)), as a bleaching agent to make new indigo dyed denim look old (Fujikawa—Japanese Patent Application Kokai No. 50-132269), to enhance the bleaching action of bleaching agents (Suzuki—Great Britain Patent No. 2 094 826), and in a process for compositions for enzymatic desizing and bleaching of textiles (Windbichtler et al., U.S. Pat. No. 2,974,001. Another example of enzymatic desizing using cellulases is provided in Bhatawadekar (May 1983) *Journal of the Textile Association*, pages 83–86.

In other industrial embodiments, the cellulase compositions can be used in the saccharification of lignocellulose biomass from agriculture, forest products, municipal solid waste, and other sources, for the production of fuels and other chemicals through fermentation, for biobleaching of wood pulp, and for de-inking of recycled print paper all by methods known to one skilled in the art.

In yet another embodiment of the subject invention, various components of the neutral and alkaline cellulase compositions can be isolated and used independently of each other. Specific components or cellulase composition enriched by certain cellulase components can be produced or isolated by chemical and physical means from mutants or specifically produced by genetic engineering methods. The cellulase system can be purified into separate components by art-recognized separation techniques including ion exchange chromatography at a suitable pH, affinity chromatography, size exclusion, chromatography and like. For example, in ion exchange chromatography, it is possible to separate the cellulase components by eluting with a pH gradient, or a salt gradient, or both. Such separations can be done by those skilled in the art having the benefit of the teachings provided herein.

Once the individual enzymatic components of the cellulase composition are fractionalized and isolated the proteins may be partially sequenced or microsequenced to design synthetic DNA or probes to isolate the gene encoding the enzymatic proteins of interest. Generally the amino terminal sequence of the protein is determined by conventional protein sequencing methods or by automated sequence (Ausubel et al., (1987) in "Current Protocols in Molecular Biology", John Wiley and Sons, New York, N.Y.). Alternatively, other regions of the protein may be sequenced in combination with chemical cleavage or enzymatic cleavage and protein separation techniques. (Ausubel et al., (1987) in "Current Protocols in Molecular Biology", John Wiley and Sons, New York, N.Y.). One of skill in the art will understand that the synthetic DNA clones or probes can be used in routine cloning techniques to isolate the genes corresponding to the enzymes present in the neutral/alkaline cellulase compositions produced by Chrysosporium.

It will be understood by one skilled in the art that nucleic and sequences obtained by this invention in the art may vary due to the degeneracy of the genetic code variations in the DNA sequence, but will still result in a DNA sequence capable of encoding the enzymatic components of the cellulase compositions. Such DNA sequences are therefore functionally equivalent to the nucleic acid sequences of the instant invention and are intended to be encompassed within the present invention. Also intended to be encompassed within this invention are nucleic acid sequences which are complementary to nucleic acid sequences capable of hybridizing to the disclosed nucleic acid sequence under a variety of conditions.

This invention further includes nucleic acid sequences encoding the enzymes of the cellulase compositions of this invention and those proteins or peptides having substantially the same function as the enzymatic proteins or peptides of this invention. Such proteins or polypeptides include, but are not limited to, a fragment of the protein, or a substitution, addition or deletion mutant. This invention also encompasses proteins or peptides that are substantially homologous to the proteins encoding the enzymes comprising the cellulase composition of this invention. The term "analog" includes any polypeptide having an amino acid residue sequence substantially identical to the sequence specifically in which one or more residues have been conservatively substituted with a functionally similar residue and which displays the functional aspects of the proteins as described herein. Examples of conservative substitutions include the substitution of one non-polar (hydrophobic) residue such as isoleucine, valine, leucine or alanine for another, the substitution of one polar (hydrophilic) residue for another such as between arginine and lysine, between glutamine and asparagine, between threonine and serine, the substitution of one basic residue such as lysine, arginine or histidine for another, or the substitution of one acidic residue, such as aspartic acid or glutamic acid for another.

Proteins or polypeptides of the present invention also include any polypeptide having one or more additions and/or deletions or residues relative to the sequence of a polypeptide whose sequence is included in the proteins of this invention so long as the requisite activity is maintained.

This invention also provides a recombinant DNA molecule comprising all or part of the nucleic acid sequences isolated by this invention and a vector. Expression vectors suitable for use in the present invention comprise at least one expression control element operationally linked to the nucleic acid sequence. The expression control elements are inserted in the vector to control and regulate the expression of the nucleic acid sequence. Examples of expression control elements include, but are not limited to, lac system, operator and promoter regions of phage lambda, yeast or other fungi promoters. Examples of promoters that may be used include, but are not limited to, glucoamylase. Additional preferred or required operational elements include, but are not limited to, leader sequence, termination codons, polyadenylation signals and any other sequences necessary or preferred for the appropriate transcription and subsequent translation of the nucleic acid sequence in the host system. It will be understood by one skilled in the art the correct combination of required or preferred expression control elements will depend on the host system chosen. It will further be understood that the expression vector should contain additional elements necessary for the transfer and subsequent replication of the expression vector containing the nucleic acid sequence in the host system. Examples of such elements include, but are not limited to, origins of replication and selectable markers. It will further be understood by one skilled in the art that such vectors are constructed using conventional methods (Ausubel et al., (1987) in "Current Protocols in Molecular Biology", John Wiley and Sons, New York, N.Y.) or may be commercially available.

Another aspect of this invention relates to a host organism into which recombinant expression vector containing all or part of the nucleic acid sequence has been inserted. The host cells transformed with the nucleic acid sequence of this invention includes eukaryotes, such as animal, plants or seeds, insect and yeast cells, fungal cells, and prokaryotes, such as E. coli or other bacteria. Examples of fungal host cells include but are not limited to Aspergillus, Trichoderma, Humicola, Penicillium, or Neurospora. The means by which the vector carrying the gene may be introduced into the cell include, but are not limited to, transformation, microinjection, electroporation, transduction, or transfection using DEAE-dextran, lipofection, calcium phosphate or other procedures known to one skilled in the art (Sambrook et al. (1989) in "Molecular Cloning. A Laboratory Manual", Cold Spring Harbor Press, Plainview, N.Y.). Alternatively, Chrysosporium cells can be transformed with the nucleic acid sequence of this invention to amplify production of cellulases by Chrysosporium.

In a preferred embodiment, expression vectors that function in fungal cells are used. Examples of such vectors include, but are not limited to plasmids, described in the patents (Ogawa; Japanese patent JP5095787 A 930420, Ozeki; Japanese patent JP7115976 A 950509, Murakami; Japanese patent JP3094690 A 910419, Ishida; Japanese patent JP3251175 A 911108, Uozumi; Japanese patent JP5268953 A 931019 DW9346 C12N-009/34 011pp, Gottschalk; German patent DE3908813 A 900920 DW9039 000 pp, Gysler; European patent EP-683228 A2 951122 DW9551 C12n-015/60 Eng 041 pp). It is preferred that the recombinant protein expression vector is introduced into fungal cells, such to ensure proper processing and modification and modification of the introduced protein.

In a further embodiment, the recombinant protein expressed by the host cells can be obtained as a crude lysate or can be purified by standard protein purification procedures known in the art which may include differential precipitation, molecular sieve chromatography, ion-exchange chromatography, isoelectric focusing, gel electrophoresis, affinity, and immunoaffinity chromatography and the like. (Ausubel et. al., (1987) in "Current Protocols in Molecular Biology" John Wiley and Sons, New York, N.Y.). In the case of immunoaffinity chromatography, the recombinant protein may be purified by passage through a column containing a resin which has bound thereto antibodies specific for the protein of interest (Ausubel et. al., (1987) in "Current Protocols in Molecular Biology" John Wiley and Sons, New York, N.Y.).

All or parts of the nucleic acid sequences of this invention can also be used as probes to isolate other homologs in other genera or strains. In a preferred embodiment the nucleic acid sequences are used to screen a Chrysosporium library; positive clones are selected and sequenced. Examples of sources from which the gene library can be synthesized include, but are not limited to species of Chrysosporium, Aspergillus, Penicillium, Humicola, Cephalosporium Tricoderma or bacteria such as Bacillus. One skilled in the art will understand the appropriate hybridization conditions to be used to detect the homologs. Conventional methods for nucleic acid hybridization, construction of libraries and cloning techniques are described in Sambrook et al., (eds) (1989) In "Molecular Cloning A Laboratory Manual" Cold Spring Harbor Press, Plainview, N.Y. and Ausubel et al., (eds) in "Current Protocols in Molecular Biology" (1987), John Wiley and Sons, New York, N.Y.

This invention also relates to mutant strains of Chrysosporium, in particular, mutant strains of *Chrysosporium lucknowense* capable of producing neutral and/or alkaline cellulases. Methods of DNA mutagenesis and screening for mutants are well known to these skilled in the art and include a variety of chemical and enzymatic methods. Examples of such methods include but are not limited to exposure of the fungi to ultraviolet light (UV), nitrous acid, N-methyl-N'-nitro-N-nitrosoguanidine (NG), and 4-nitroquinoline-N-oxide (4NQO). (Leninger (1972) *Biochemistry*, Worth Publishers Inc., N.Y.; Jeffrey H. Miller (1972) "Experiments in Molecular Genetics. Cold Spring Harbor Laboratory, Cold Springs Harbor, N.Y.). Preferred methods, include UV and NG. By way of example, mutant strains of Chrysosporium capable of producing increased levels cellulase compositions exhibiting enzymatic activity at neutral and or alkaline pH's may be generated by UV mutagenesis. By way of examples mutants may be produced by exposure of the fungal spores to UV light for a period of about 10 to about 180 seconds, preferably 45 to about 90 seconds, and most preferably 65 to 75 seconds. Mutageneses involving NG may involve varying the concentration of the NG and exposure time. By way of example NG, at about 13 milligrams/liter (mg/L) to about 400 mg/L of NG may be used for a period of exposure of about 15 minutes to about 120 minutes. Alternative methods for generating mutants include techniques in the field of molecular biology. Examples of such techniques include, but are not limited to, oligonucleotide directed mutagenesis, linker scanning mutations or oligonucleotide directed mutagenesis using polymerase chain reaction (Ausubel (1987) Current Protocols in Molecular Biology).

Screening and selection of mutant Chrysosporium clones exhibiting improved cellulase production can also be performed by conventional methodology. Examples of selection criteria for screening mutants includes, but is not limited, to the ability of the fungal colony to breakdown cellulase as evidenced by cellulose clearing by the fungi grown on media plates containing cellulose and increased growth rate on media containing cellulose. By way of example, after mutagenesis the fungal sample may be plated on agar plates containing cellulose by conventional methodology. Colonies exhibiting increased growth and cellulose clearing (as is evidenced by clearing of the media surrounding the isolate) may be selected. However, any other assay for cellulose clearing may be used. Once a mutant is isolated the stock or spores derived from the mutant may be maintained by conventional methodology. The mutants isolated by this method may be cultured or fermented under the conditions described herein and above for the wild type strains of Chrysosporium. The individual enzymatic components of the cellulase composition produced by the mutants may be partially sequenced or microsequenced to design synthetic to isolate the genes encoding the enzymatic proteins of interest. Thus, this invention relates to the nucleic acid sequences encoding the cellulase enzymes produced by the Chrysosporium mutants and to the enzymes themselves. In yet another embodiment of this invention, the mutants isolated may be subjected to further mutagenisis and screened by the methods described herein above.

All books, patents or articles references herein are incorporated by reference. The following examples illustrate various aspects of the invention but in no way are included to limit the invention. All percentages are by weight and all solvent mixture proportions are by volume unless otherwise noted.

MATERIALS AND METHODS

Enzyme assays. The assay for CMCase, used carboxymethyl cellulose as the enzymatic substrate, measured the initial rate of hydrolysis, and quantified the amount of reducing sugars released according to the method of Somogyi and Nelson. The method is described in *Methods in Enzymology*, Vol. 160A, pp. 102–104. Endo-1,4-β-glucanase activity was assayed viscometrically as a rate of the decrease of viscosity of soluble substrate CMC according to *Bioorganicheskaya Khimia*, Vol. 6, pp. 1225–1242 (endoviscometric assay). Filter paper activity (FPA) or total cellulase activity used filter paper as the substrate and estimated the activity required to release 2 mg glucose from a 50-mg sample of filter paper. The assay is based on the Commission on Biotechnology (IUPAC) for the measurement for total cellulase activity or true cellulase and is described in *Methods in Enzymology*, Vol. 160A, pp. 94–97. Avicelase activity was estimated as initial rate of reducing sugar formation during hydrolysis if Avicell-cellulose (as described in *Bioresource Technology*, Vol. 52, pp. 119–124). The assay of cellobiase used cellobiose as the substrate and measured the amount of glucose released (described in *Methods in Enzymology*, Vol. 160A, pp. 111–112). The assay of β-glucosidase activity used p-nitrophenyl-β-D-glucoside as the substrate (described in *Methods in Enzymology*, Vol. 160A, pp. 109–1100). The protein was determined by Lowry method (according to *Journal of Biological Chemistry*, Vol. 193, pp. 165–175). The assay of RBB-CMCase is based on determination of the dye release from soluble substrate RBB-CMC (CMC, dyed with Remazolbrilliant Blue), reference to assay—see Megazyme (Australia) Ltd., Product Information Bulletin, April, 1995.

EXAMPLE 1

Isolation of C1 Strain

The strain was isolated from samples of forest alkaline soil from Sola Lake, Far East of Russian Federation (Pacific Coast of Russia, about 5000 miles east from Moscow). A mixed soil sample was collected from 10 different sites. One gram of each sample was transferred into a flask with 100 ml sterile tap water and sonicated with an ultrasonic dispenser for 1 minute (0.44 Amp, 22 KHz). The suspension (diluted 1:500) was inoculated into petri dishes with Czapek medium (pH 5.5–6.0) containing 100 mg/L streptomycin. The study was conducted in three replicates. Colonies of various color shape and size were identified for a second isolation step. Further isolation of the sample was performed on plates with Czapek media, malt agar, potato dextrose agar, or Getchinson saline medium pH 7.5 (Table 2). Plates were incubated at about 28° C. for several days. Selection for cellulase producers was performed on cellulose agar plates which contained the components shown in Table 1. Preparation of amorphous cellulose is described in *Methods in Enzymology* vol. 160A.

TABLE 1

Cellulose agar plates

| Ingredients | g/L |
|---|---|
| $KH_2PO_4$ | 1 |
| KCl | 0.1 |
| $MgSO_4.7H_2O$ | 0.3 |
| NaCl | 0.1 |
| $FeCl_3$ | 0.01 |
| $NaNO_3$ | 2.5 |
| Amorphous cellulose | 5 |
| Agar | 15 |
| pH | 7.5 |

The plates were incubated for 3–7 days at 28° C. The formation of light clearing halos around the colonies indicated cellulase activity. One strain, designated herein as C1, that exhibited significant levels of cellulase activity was chosen for additional study. The strain was deposited at the All-Russian Collection of Microorganisms of Russian Academy of Sciences, (VKM), abbreviation in English—RCM), Bakhrushina St. 8: Moscow, Russia, 113184 under the Budapest Treat on Aug. 29, 1996, as *Chrysosporium lucknowense* Garg 27K, VKM-F 3500 D).

EXAMPLE 2
Characterization of C1 Strain

Growth of the C1 strain on potato dextrose agar gives colonies of 55–60 mm diameter after 7 days. C1 colonies exhibit a white-cream color, the surface is velvet-like and has a slightly raised center. The edge of the colonies is a flat, thin and fibereil. The back side of the colonies has a light cream color.

The mycelium has hyaline and is slightly branched and smooth. The hyphae are thin-walled. Air hyphae are septate and form spores of 2.0–3.0 micrometers width; the substrate hyphae are sterile.

The conidia are terminal and lateral. No intercalary conidia were found. The majority of conidia are connected with hyphae through short stems or short side branches. The conidia are separated but adjacent. Conidia are hyaline, thin-walled, oval or clavate, and single cellular. Their size varies from 4 to 10 micrometers in diameter.

The C1 strain can be maintained on malt extract agar (at 4° C.), and transferred each six months. Maintenance in liquid nitrogen and by lyophilization is also possible. The C1 strain is haploid, filamentous, can grow on agar plates with growth restricting agents like bovinebile (1.5%), and produces spores.

EXAMPLE 3
Classification of C1 Strain

According to Sutton classification (Van Dorschot, C.A.N. [1980] "A revision of Chrysosporium and allied genera," in *Studies in Mycology*, No. 20, Centraaddbureau voor Schimmelcultures, Baarn, The Netherlands, pp. 1–36), the C1 strain of the subject invention belongs to the order of Hyphomycetales, family of Moniliaceae, genus of Chrysosporium, species of *Chrysosporium lucknowense* Garg 1966. This classification was based on observation of the following characteristics of the C1 strain:

1. Signs of Hyphomycetales order. Conidia are produced directly on mycelium, on separate sporogenous cells or on distinct conidiophores.

2. Signs of Moniliaceae family. Both conidia and conidiophores (if present) are hyaline or brightly colored; conidiophores are single or in loose clusters.

3. Signs of Chrysosporium Corda 1833 genus. Colonies are usually spreading, white, sometimes cream-colored, pale brown or yellow, felty and/or powdery. Hyphae are mostly hyaline and smooth-walled, with irregular, more or less orthotopic branching. Fertile hyphae exhibit little or no differentiation. Conidia are terminal and lateral, thallic, borne all over the hyphae, sessile or on short protrusions or side branches, subhyaline or pale yellow, thin- or thick-walled, subglobose, clavate, pyriform, orobovoid, 1-celled, rarely 2-celled, truncate. Intercalary conidia are sometimes present, are solitary, occasionally catenate, subhyaline or pale yellow, broader than the supporting hyphae, normally 1-celled, truncate at both ends. Chlamydospores are occasionally present.

4. Signs of *Chrysosporium lucknowense* Garg 1966 species. Colonies attain 55 mm diameter on Sabouraud glucose agar in 14 days, are cream-colored, felty and fluffy; dense and 3–5 mm high; margins are defined, regular, and fimbriate; reverse pale yellow to cream-colored. Hyphae are hyaline, smooth- and thin-walled, little branched. Aerial hyphae are mostly fertile and closely septate, about 1–3.5 mm wide. Submerged hyphae are infertile, about 1–4.5 mm wide, with the thinner hyphae often being contorted. Conidia are terminal and lateral, mostly sessile or on short, frequently conical protrusions or short side branches. Conidia are solitary but in close proximity to one another, 1–4 conidia developing on one hyphal cell, subhyaline, fairly thin- and smooth-walled, mostly subglobose, also clavate orobovoid, 1-celled, 2.5–11×1.5–6 mm, with broad basal scars (1–2 mm). Intercalary conidia are absent. Chlamydospores are absent.

5. Description of C1 strain. Colonies grow to about 55–60 mm diameter in size on potato-dextrose agar in about 7 days; are white-cream-colored, felty, 2–3 mm high at the center; margins are defined, regular, fimbriate; reverse pale, cream-colored. Hyphae are hyaline, smooth- and thin-walled, little branched. Aerial hyphae are fertile, septate, 2–3 mm wide. Submerged hyphae are infertile. Conidia are terminal and lateral; sessile or on short side branches; absent; solitary, but in close proximity to one another, hyaline, thin- and smooth-walled, subglobose, clavate or obovoid, 1-celled, 4–10 mm. Chlamydospores are absent. Intercalary conidia are absent.

Conclusion. C1 is a strain of *Chrysosporium lucknowense* Garg 1966. For convenience the cellulase made by this strain is referred to herein as "C1" or "C1 cellulase."

EXAMPLE 4
Assay for Cellulase Activity

The C1 strain was grown in 800 ml shake flasks rotated at 220 rpm and incubated at 28° C. The C1 strain was grown in saline Getchinson medium (See Table 2) (pH 7.5) containing 5 g/L of various nutrients, and in some cases with 2 g/L microcrystalline cellulose. One hundred ml of media were added to each flask.

TABLE 2

Getchinson medium for shake flasks

| | g/L |
|---|---|
| $KH_2PO_4$ | 1 |
| KCl | 0.1 |
| $MgSO_4.7H_2O$ | 0.3 |
| NaCl | 0.1 |
| $FeCl_3$ | 0.01 |
| $NaNO_3$ | 2.5 |

Combinations of glucose and microcrystalline cellulose, dextrose and microcrystalline cellulose, glycerol and microcrystalline cellulose, lactose and microcrystalline cellulose resulted in very low growth, formation of large aggregates of mycelium, and in the absence of cellulase activities (CMC-ase assay). The results are presented in Table 3. Additions of nitrogen organic sources, i.e., peptone, corn steep liquor, or yeast extract enhanced growth and cellulase production and did not result in mycelium aggregates.

Lactose and yeast extract gave the highest cellulase production by C1. Similar results were obtained when the lactose and yeast extract were substituted with 25 g/L sweet beet pulp, 15 g/L barley malt, and 5 g/L wheat bran.

TABLE 3

Effect of carbon and nitrogen sources on CMC-ase activity of C1 (shake flasks results)

| Substrate | CMC-ase activity (units/ml) at pH 7.0 | | |
|---|---|---|---|
| | 3 | 5 | 7 |
| Glucose + cellulose | 0 | 0 | 0 |
| Dextrose + cellulose | 0 | 0 | 0 |
| Glycerol + cellulose | 0 | 0 | 0 |
| Lactose + cellulose | 0 | 0 | 0 |
| Lactose + corn steep liquor | 0 | 0 | 0.9 |
| Lactose + peptone | 10.7 | 7.4 | 14.8 |
| Lactose + yeast extract | 0 | 18.5 | 10.0 |
| Cellulose + peptone | 0.3 | 1.2 | 1.6 |
| Cellulose + corn steep liquor | 1.9 | 2.8 | 5.5 |

EXAMPLE 5

Production of Cellulase for Stone Wash Tests

1. Production in shake flasks. C1 strain was grown in 800 ml shake flasks rotated at 220 rpm and incubated at 28° C. for seven days. The growth medium 100 ml per flask was saline Getchinson medium (see Table 2) (pH 7.5) containing 25 g/L sweet beet pulp, 15 g/L barley malt, and 5 g/L wheat bran. The cell mass was separated by centrifugation and the cell-free supernatant was lyophilized and stored for further tests. C1 cellulase preparation #s 47.1.1 to 47.15.1 were produced in this manner. C1 preparation #47.16.1 was produced by the same manner, but cell-free supernatant after centrifugation was ultrafiltrated using a 10 kDa cutoff membrane before lyophilization. C1 preparation #'s 47.18.1 to 47.22.1 were produced by the same manner in shake flasks with Getchinson medium, but containing lactose (0.5% w/v) and peptone (0.5% w/v) instead of sweet beet pulp, barley malt and wheat bran. The cell mass was separated by centrifugation and the cell free supernatant was lyophilized and stored for further tests. Preparation #'s 47.1000, 47.1001, 47.2000 & 47.2001 were produced in shake flasks by the same manner as preparation #'s 47.1.1–47.15.1 except that they were produced using other Chrysosporium strains. Specifically, 47.2001 was produced by *Chrysosporium pannorum*, preparation 47.2000 was produced by *Chrysosporium pruinosum*, preparation 47.1001 was produced by *Chrysosporium keratinophilim* and preparation 47.1000 was produced by *Chrysosporium queenslandicum* (see Example 8). The protein content and activity fingerprints of these C1 preparations are shown in Table 4.

TABLE 4

Protein content and activity fingerprints of C1 preparations and preparation #'s 47,1000, 47.1001, 47.2000 & 47.2001 which were prepared from other species of Chrysosporium sp.

| Preparation # | Protein, % | FPA, FPU/g | CMC-ase, U/g | Endo (visc), U/g | Avicelase, U/g | β-Glucosidase, U/g |
|---|---|---|---|---|---|---|
| 47.1.1 | 22 | 13 | 170 | 120 | 23 | 135 |
| 47.2.1 | 26 | 14 | 137 | 110 | 22 | 190 |
| 47.3.1 | 15 | 19 | 140 | 128 | 18 | 198 |
| 47.4.1 | 18 | 23 | 150 | 133 | 55 | 220 |
| 47.5.1 | 16 | 20 | 179 | 120 | 71 | 185 |
| 47.6.1 | 17 | 22 | 224 | 134 | 82 | 280 |
| 47.7.1 | 8 | 4 | 78 | 123 | 10 | 22 |
| 47.8.1 | 22 | 14 | 168 | 123 | 19 | 124 |
| 47.9.1 | 28 | 15 | 204 | 174 | 23 | 151 |
| 47.10.1 | 24 | 11 | 181 | 185 | 16 | 147 |
| 47.11.1 | 28 | 16 | 234 | 191 | 25 | 269 |
| 47.12.1 | 26 | 14 | 167 | 138 | 20 | 178 |
| 47.13.1 | 25 | 9 | 137 | 110 | 13 | 141 |
| 47.14.1 | 15 | 6 | 39 | 33 | 9 | 59 |
| 47.15.1 | 14 | 6 | 95 | 44 | 10 | 75 |
| 47.16.1 | 16 | 10 | 146 | 39 | 15 | 107 |
| 47.17.1 | 7 | 3 | 100 | 34 | 5 | 29 |
| 47.18.1 | 10 | 30 | 120 | 38 | 10 | 42 |
| 47.19.1 | 14 | 4 | 28 | 10 | 4 | 11 |
| 47.20.1 | 14 | 6 | 17 | 5 | 1 | 9 |
| 47.21.1 | 13 | 3 | 34 | 5 | 3 | 9 |
| 47.22.1 | 14 | 5 | 35 | 6 | 3 | 10 |
| 47.1000 | 18 | 4 | 31 | 35 | 6 | 89 |
| 47.1001 | 13 | 6 | 103 | 38 | 10 | 66 |
| 47.2000 | 10 | 3 | 78 | 31 | 7 | 67 |
| 47.2001 | 13 | 3 | 45 | 39 | 7 | 4 |
| 47.0325 | 50 | 155 | 4965 | 964 | 184 | 248 |
| 47.0528 | 67 | 111 | 13500 | 1782 | 232 | 423 |

2. Production in fermentors. C1 cellulase was produced in a 10-L "ANKUM-1M" fermentor with Getchinson medium, lactose (0.5% w/v), peptone (0.5% w/v), and chloramphenicol (50 mg/mL). Initial volume of the nutrition medium was 7.0 L, final volume after fermentation was 7.3 L. The dissolved oxygen concentration (DO), agitation speed, aeration level, temperature, and pH were controlled. Fermentation was carried out as a batch-mode. the temperature of the fermentation was controlled at 28° C. The initial pH was 7.5 and was later maintained at that level by addition of $NH_4OH$ (12% w/v). The aeration was at 4–5 L/minute and agitation at 400–500 rpm. The DO was maintained at above 50%. Samples (30 ml) were taken for analysis every 8 hours. At the end of fermentation, fungal biomass was separated by centrifugation (10,000 g, room temperature, 20 minutes), and culture filtrate was lyophilized and stored for further tests. The results are shown in table 5. Cellulase preparation #47.17.1 was produced in this manner. Protein content and activity fingerprint of this C1 preparation is shown in Table 4.

TABLE 5

Production of C1 cellulase in 10-L fermentor

| Time (h) | DO (%) | Reducing sugars (g/L) | CMC-ase (U/mL) |
|---|---|---|---|
| 0 | 100 | 4.8 | 0 |
| 8 | 90 | 4.7 | 0 |
| 16 | 54 | 4.4 | 0 |
| 24 | 66 | 1.2 | 4 |
| 32 | 70 | 0.4 | 10 |

TABLE 5-continued

| | Production of C1 cellulase in 10-L fermentor | | |
|---|---|---|---|
| Time (h) | DO (%) | Reducing sugars (g/L) | CMC-ase (U/mL) |
| 40 | 73 | 0.3 | 11.5 |
| 48 | 70 | 0.1 | 5 |
| 56 | 70 | 0 | 1 |

3. Production of C1 Preparation #'s 47.0325 and 47.0528. C1 cellulase preparation #47.0325 was produced using the wild type C1 strain, preparation #47.0528 was produced using an improved mutant obtained from the wild type C1 strain. These preparations were grown up fermentors under the conditions described in Examples 13 and 15. Preparation 47.0325 was produced using a batch fermentation and 47.0528 was produced using a fed batch fermentation protocol.

4. Preparation of Humicola wild type preparation #'s 14.22.1 & 14.23.1 The wild type *Humicola grisea* var. *thermoidea* preparation #14.22.1 was produced from the ATCC 16453 strain and the wild type *Humicola insolens* preparation #14.23.1 was produced from the ATCC 16454 strain. These Humicola wild type preparations were produced in shake flasks using the same method as described above for (Production in shake flasks) of C1 preparation #'s 47.1.1–#47.15.1.

EXAMPLE 6

Comparison of C1 to Other Neutral Cellulases

The FPA, CMCase and endoglucanase activities of C1 enzyme preparation #47.0528 were compared to commercial *Humicola insolens* (Denimax XT) and to wild ATCC-type Humicola (preparation #'s 14.22.1 *Humicola grisea* var. *thermoidea* (ATCC 16453) & 14.23.1 *Humicola insolens* (ATCC 16454) neutral cellulases. The results are given in the Table 6. The total activities of C-1 #47.0528 are clearly higher than those of neutral cellulases from wild type Humicola and from commercial *Humicola insolens* preparation. The specific CMCase and endoglucanase activities (as units per gram of dry preparation or units per gram of protein) of C-1 47.0528 are higher than those of all tested Humicola preparations listed in Table 6. The specific FPA of C-1 #47.0528 is higher than the specific FPA of Humicola wild type preparations #14.22.1 & 14.23 and slightly lower than the specific FPA of the Humicola insolen commercial product Denimax XT. The pH and thermal stability of C1 cellulase was similar to Denimax XT.

TABLE 6

Comparison of C1 and Humicola cellulases.

| | Pro- tein % | units/1 gram dry preparation | | | units/1 gram of protein | | |
|---|---|---|---|---|---|---|---|
| | | CM-Case | FPA | Endo (visc) | CMCase | FPA | Endo (visc) |
| C1 (47.0528) | 67 | 111 | 13,500 | 1782 | 165 | 20,115 | 2,655 |
| Humicola sp. (# 14.23.1) | 10 | 2 | 28 | 30 | 20 | 280 | 300 |
| Humicola sp. (# 14.23.1) | 10 | 1 | 11 | 19 | 10 | 110 | 190 |
| Denimax XT commercial | 13 | 25 | 450 | 99 | 192 | 3,460 | 761 |

(*) Activities were measured at pH 5.0 and 50° C.

EXAMPLE 7

The Effect of pH and Temperature on Activity and Stability of C1 FPA and CMC-ase Activities The FPA and CMC-ase activities of C1 exhibit optimal stability and activity at about pH 6–7 and about 50–60° C.; the pH optimum for CMC-ase activity is about 6.5, and the optimum temperature is about 55° C. (see Tables 8,9). At pH 8.0 (50° C.), CMC-ase possesses 80% activity, and FPA— 78% activity, at pH 9.0 (50° C.), CMC-ase possesses 65% activity, and FPA—52% activity (see Table 7.).

TABLE 7 the effect of pH on FPA and CMCase activities of C1 cellulase (#47.19.1) at 50° C.

| pH (50° C.) | FPA (%) | CMC-ase (%) |
|---|---|---|
| 4.0 | 50 | 60 |
| 4.5 | 68 | 70 |
| 5.0 | 75 | 78 |
| 5.5 | 80 | 80 |
| 6.0 | 92 | 90 |
| 6.5 | 100 | 100 |
| 7.0 | 95 | 95 |
| 7.5 | 90 | 92 |
| 8.0 | 78 | 80 |
| 8.5 | 60 | 75 |
| 9.0 | 52 | 65 | the incubation time for the FPA assay was 60 minutes, the incubation time for CMCase assay was 5 minutes.

TABLE 8

The effect of temperature on FPA and CMC-ase activities of C1 cellulase (#47.19.1), at pH 7.0

| Temperature (C.) | FPA (%) | CMC-ase (%) |
|---|---|---|
| 40 | 45 | 50 |
| 45 | 60 | 55 |
| 50 | 70 | 65 |
| 55 | 100 | 100 |
| 60 | 70 | 60 |
| 65 | 40 | 30 |
| 70 | 20 | 25 | the incubation time for the FPA assay was 60 minutes, the incubation time for the CMCase assay was 5 minutes.

TABLE 9

Stability of CMC-ase of C1 cellulase (# 47.19.1) at 50° C.

| | CMC-ase activity remained (%) | | | |
|---|---|---|---|---|
| Time (h) | pH 5.1 | pH 7.2 | pH 7.7 | pH 8.5 |
| 0 | 100 | 100 | 100 | 100 |
| 0.5 | 100 | 98 | 95 | 85 |
| 1 | 100 | 95 | 93 | 55 |
| 2 | 100 | 82 | 78 | 32 |
| 3 | 100 | 78 | 65 | 25 |
| 5 | 100 | 75 | 45 | 15 |

The CMC-ase of C1 exhibits high stability at optimal pH and temperature: For Example; at pH 7.2 and 50° C. CMCase possesses 95% activity after 1 hour and 75% activity after 5 hours, at pH 7.7 and 50° C. CMCase possesses 93% activity after 1 hour and 45% activity after 5 hours (See Table 9.).

EXAMPLE 8
Neutral and or Alkaline Cellulase Activity/Performance Demonstrated in Other Strains of the Same Genera of Chrysosporium Various strains of the Chrysosporium genus were tested for cellulase production. The full names and origins of these strains are described below.

Strains obtained from the American Type Culture Collection (ATCC), Rockville, Md., include:

1. ATCC 44006 *Chrysosporium lucknowense*
2. ATCC 34151 *Chrysosporium pannorum*
3. ATCC 24782 *Chrysosporium pruinosum*

Strains obtained from the Russian Collection of Microorganisms (VKM) include:

1. VKMF-2119 *Chrysosporium keratinophilum*
2. VKMF-2875 *Chrysosporium keratinophilum*
3. VKMF-2120 *Chrysosporium lobatum*
4. VKMF-2121 *Chrysosporium merdarium*
5. VKMF-2116 *Chrysosporium queenslandicum*
6. VKMF-2117 *Chrysosporium queenslandicum*
7. VKMF-2877 *Chrysosporium tropicum*

Two types of growth media were used in this study: medium A—Getchinson with sugar beet press, barley malt, and wheat bran; and medium B—Getchinson with peptone and lactose. The compositions of the media are described in Table 11.

TABLE 11

Media for flasks studies

| Medium A | g/L | Medium B | g/L |
|---|---|---|---|
| $K_2HPO_4$ | 1 | $K_2HPO_4$ | 1 |
| KCl | 0.1 | KCl | 0.1 |
| $MgSO_4.7H_2O$ | 0.3 | $MgSO_4.7H_2O$ | 0.3 |
| NaCl | 0.1 | NaCl | 0.1 |
| $FeCl_3$ | 0.01 | $FeCl_3$ | 0.01 |
| $NaNO_3$ | 2.5 | $NaNO_3$ | 2.5 |
| Sweet beet pulp | 25 | Lactose | 5 |
| Barley malt | 15 | Peptone | 5 |
| Wheat bran | 5 | pH | 7.5 |
| pH | 7.5 | | |

The strains were grown in shake flasks at 220 rpm and at 28° C. Samples of each strain grown in Medium A were taken for analysis after 6 and 7 days of culture. Samples of strains grown in Medium B were taken after 5 days in culture. All samples were assayed for CMC-ase activity at pH 5 and 7. The results of the CMC-ase assay are shown in Table 12.

TABLE 12

Cellulase production by different strains of Chrysosporium

| | medium A (6 days) | | | medium A (7 days) | | | medium B (5 days) | | |
|---|---|---|---|---|---|---|---|---|---|
| | | CMC-ase | | | CMC-ase | | | CMC-ase | |
| Strains | RS | pH 5 | pH 7 | RS | pH 5 | pH 7 | RS | pH 5 | pH 7 |
| 1. VKMF 2117 | 2.7 | 0 | 0.46 | 2.6 | 0.00 | 0.00 | 2.3 | 0.21 | 0.09 |
| 2. VKMF 2116 | 1.1 | 0.22 | 0.04 | 0.2 | 0.38 | 0.61 | 4.0 | 0.58 | 0.59 |
| 3. VKMF 2121 | 1.9 | 0 | 0.57 | 1.1 | 0.25 | 0.10 | 2.5 | 0.25 | 0.09 |
| 4. ATCC 24782 | 3.4 | 0.33 | 1.40 | 1.9 | 1.85 | 0.11 | 3.0 | 1.10 | 0.06 |
| 5. ATCC 34151 | 1.0 | 1.54 | 0.90 | 0.9 | 0.17 | 0.20 | 4.3 | 0.81 | 0.90 |
| 6. ATCC 44006 | 4.4 | 0.21 | 0.49 | 2.0 | 0.68 | 0.34 | 2.5 | 1.29 | 0.06 |
| 7. VKMF 2119 | 4.1 | 0 | 0.08 | 2.7 | 0.29 | 0.00 | 3.8 | 0.95 | 0.04 |
| 8. VKMF 2120 | 4.5 | 0 | 0.17 | 2.3 | 0.23 | 0.00 | 2.3 | 0.12 | 0.00 |
| 9. VKMF 2875 | 1.6 | 0 | 1.01 | 1.7 | 0.00 | 0.00 | 3.8 | 1.96 | 0.05 |
| 10. VKMF 2877 | 2.4 | 0 | 0.03 | 0.8 | 0.22 | 0.00 | 5.0 | 0.43 | 0.00 |
| 11. C1 (VKMF 3500D) | 2.9 | 1.70 | 1.65 | nt | nt | nt | 0.1 | 0.89 | 0.80 |

RS = concentration of reducing sugars in the fermentation medium at the end of fermentation, g/L (Nelson-Somogyi method).
pH 5, pH 7 = the values of pH under which the CMC-ase activity of the fermentation broth was assayed.
CMC-ase activity in U/ml.
nt = not tested In the cases of strains ATCC 34151 *Chrysosporium pannorum*, ATCC 24782 *Chrysosporium pruinosum*, VKMF-2875 *Chrysosporium keratinophilum*, VKMF 2116 *Chrysosporium queenslandicum* the cell mass was separated by centrifugation and cell free supernatant concentrated from 5 liters to 0.5 liter by ultrafiltration using 10 kDa cut-off membrane. Then the ultrafiltrated concentrate was lyophilized and stored for tests.

The following #-s of cellulase dry preparations were used:

| | |
|---|---|
| 47.2001 - ATCC 34151 | *Chrysosporium pannorum*, |
| 47.2000 - ATCC 24782 | *Chrysosporium pruinosum*, |
| 47.1001 - VKMF-2875 | *Chrysosporium keratinophilum*, |
| 47.1000 - VKMF 2116 | *Chrysosporium queenslandicum*. |

Protein content and activity fingerprints of these preparations are given in Table 4.

EXAMPLE 9
Stone Wash Tests

A. Tests with 2-L special washing machine. This system assesses the stone wash performance characteristics related to abrasion and backstaining using only small amounts of enzyme.

Desizing. Forty pieces (30 g each, 25×20 cm) of denim fabric (roll) (1.2 kg) were desized in a household washer at 60° C. for 20 minutes using a fabric:liquor ratio of 1:6 (7.2 L) and 0.5 g/L (3.6 g) Sandoclean PC liquid (nonionic washing and wetting agent on base of ethyoxylated fatty alcohols with an average of 6 moles of ethylene oxide, 1 g/L (7.2 g) Sirrix 2UD (acidic buffered sequestration) and 1 g/L (7.2 g) Bactosol TK liquid (high temperature stable alpha-amylase) at a pH of about 5 to 6. After 20 minutes, the liquor was drained and the pieces washed for 5 minutes with cold water (14 L) liquid ratio 1:10. The pieces were dried at 40° C. and used as a stock of comparable samples for the determination of cellulase activity The cellulase treatment of the garment pieces was carried out in a washing machine consisting of an inner drum of 29 cm diameter drum—10.6 l total volume (drum rotates at 20 rpm—five turns left—five turns right). Each piece of fabric was sewn together with 4 rubber stoppers prior to the cellulase treatment to give a garment package that ensured that the mechanical effect occurred mainly on the darker outer side of the garment. Each drum was filled with one package and 10 additional rubber stoppers.

The general wash conditions were: 30 g desized denim jean fabric, cellulase in 0.02 M citrate buffer, 50° C., 60 minutes, garment:liquor ratio 1:4. After the cellulase treatment the package was washed with hot water (50° C.) (garment:liquid ratio 1:20) for 5 minutes and dried for evaluation.

Application trials were conducted using various C1 cellulase preparations along with other cellulase preparations prepared from different species of Chrysosporium as well as the commercial Novo Nordisk neutral cellulase products, Denimax XT (U.S. Pat. No. 4,435,307) and Ultra MG (WPO 91/17243). These application trials were set up to evaluate the stone wash performance characteristics of C-1 as well as several other species of Chrysosporium cellulases vs Novo's commercial neutral cellulases. The trials were run at neutral and alkaline pH's (6.5, 6.7, 7.0, and 8.0). The results are presented in Table 13. Garments treated with various C1 and other Chrysosporium cellulase preparations showed similar wash performance characteristics to those of the commercial neutral cellulases Denimax XT and Denimax Ultra MG. The C-1 and other Chrysosporium cellulase preparations showed good softening effect, bleaching/overall shade reduction, abrasion levels as well as low backstaining values when run under neutral and alkaline pH conditions.

Datacolor measurement is based on the degree of lightness of the sample (reflectance). The sample is exposed to white light (2 pulsed Xenon flash lamps) and the remission is detected between 400 and 700 nm with 16 diodes. Reflectance from the front side, the higher value the more abrasion. Reflectance from the back side, the higher value the more backstaining.

TABLE 13

Enzyme Wash With Special 2 Liter Machine (135 grams of denim per run)

| Enzyme | Amount g | % OWG | CMCase U/g | /run | Endo (visc) U/g | /run | °C. | Liquor ratio | pH | Time (min) | Buffer | Datacolor Abrasion | Datacolor Backstng |
|---|---|---|---|---|---|---|---|---|---|---|---|---|---|
| C-1 47.11.1 | 1.995 | 1.5 | 234 | 474 | 191 | 381 | 50 | 1:11 | 7.2 | 60 | 0.02MP | 13.1 | 1.8 |
| Denimax XT | 0.133 | 0.10 | 450 | 60 | 99 | 13 | 50 | 1:11 | 7.0 | 60 | 0.02MP | 13.1 | 2.4 |
| C-1 47.12.1 | 2.100 | 1.5 | 167 | 338 | 138 | 290 | 50 | 1:11 | 6.7 | 60 | 0.02MP | 14.2 | 1.8 |
| Denimax XT | 0.420 | 0.30 | 450 | 182 | 99 | 42 | 50 | 1:11 | 6.6 | 60 | 0.02MP | 14.0 | 2.3 |
| C-1 47.9.1 | 3.29 | 2.44 | 204 | 671 | 174 | 572 | 50 | 1:11 | 6.7 | 60 | 0.02MP | 17.1 | 1.8 |
| C-1 47.16.1U | 2.3 | 1.7 | 146 | 336 | 39 | 90 | 50 | 1:11 | 6.7 | 60 | 0.02MP | 16.2 | 2.3 |
| 47/1000.1 | 7.0 | 5.19 | 48 | 336 | 14 | 98 | 50 | 1:11 | 6.5 | 60 | 0.02MP | 12.9 | 2.1 |
| 47/2001.1 | 7.15 | 5.30 | 47 | 336 | 20 | 143 | 50 | 1:11 | 6.5 | 60 | 0.02MP | 14.7 | 1.7 |
| Denimax UltraMG | 0.132 | 0.10 | 134 | 18 | 243 | 32 | 50 | 1:11 | 7.3 | 60 | 0.02MP | 14.1 | 3.5 |
| C-1 47.19.1 | 7.14 | 5.29 | 28 | 200 | 9 | 64 | 50 | 1:11 | 6.5 | 60 | 0.02MP | 14.7 | 1.9 |
| C-1 47.0325 | 0.068 | 0.05 | 4965 | 338 | 964 | 66 | 50 | 1:11 | 7.0 | 60 | 0.02MP | 15.1 | 2.3 |
| Denimax XT | 1.0 | 0.74 | 450 | 450 | 99 | 99 | 50 | 1:11 | 6.5 | 60 | 0.02MP | 19.1 | |
| C-1 47.0528 | 0.08 | 0.05 | 4800 | 384 | 1782 | 143 | 50 | 1:11 | 6.5 | 60 | 0.02MP | 18.5 | 2.8 |
| C-1 47.0325 | 0.136 | 0.10 | 4965 | 675 | 964 | 131 | 50 | 1:1i | 6.0 | 60 | 0.02MP | 18.3 | 3.8 |
| C-1 47.0325 | 0.136 | 0.10 | 4965 | 675 | 964 | 131 | 50 | 1:11 | 7.0 | 60 | 0.02MP | 18.9 | 3.2 |
| C-1 47.0325 | 0.136 | 0.10 | 4965 | 675 | 964 | 131 | 50 | 1:11 | 8.0 | 60 | 0.02MP | 16.7 | 2.5 |
| Humicola 14.22.1 | 9.18 | 6.80 | 28 | 257 | 30 | 275 | 50 | 1.11 | 6.7 | 60 | 0.02MP | 14.9 | 1.3 |
| Humicola 14.23.1 | 9.18 | 6.80 | 11 | 101 | 19 | 174 | 50 | 1:11 | 6.7 | 60 | 0.02MP | 12.5 | 1.5 |
| T. reesei CP | 0.30 | 0.22 | 9190 | 2737 | 2000 | 600 | 50 | 1:11 | 4.8 | 60 | 0.02CA | 17.5 | 8.0 |
| Blank | 0.00 | 0.00 | 0 | 0 | 0 | 0 | 50 | 1:11 | 6.5 | 60 | 0.02MP | 9.1 | n/a |

0.02MP = Phosphate Buffer System
0.01CA = Citric Acid Buffer System
T. reesei CP = Commercial acid cellulase product produced from *Trichoderma reesei*.
Datacolor Abrasion = reflectance from the front side, the higher the values, the more abrasion, blank = 9.1
Datacolor Backstng = reflectance from the back side, the lower the values, the lower the back staining
% OWG = for example for 1% OWG, 1 lb of enzyme is used on 100 lbs of garment B. Tests with 35 lb washing machine. Application Trials were run in a 35 lb washing machine (35 lb washing machine brand is Milnor—washer RPM is 30). Load size is 2400 g (3 garments), garments used are Levi's 505 jeans. Water level for cellulase bath is 15 L for a liquor ratio of 6.25:1 (low). The water level for all other baths is 24 L for a liquor ratio of 10:1 (Med). The buffering system used is MAP—monoammonium phosphate and DAP—diammonium phosphate to maintain the pH of 6.7 during the cellulase bath. In Trials 4, 5, 6 & 7 a nonionic detergent was added to the cellulase bath, it is known that adding a detergent to the cellulase bath will help in reducing the backstaining on the garments. Zeke is a desizing product. SSCE is Superscour, a nonionic detergent (Zeke and Super Scour are commercial specialty textile chemical products offered by CPN International, Ltd., Inc of Jupiter, Fla.). One Example of the Wash Formulas used in these trials is Trial 2. below;

| Wash Formula - Trial 2. (C-1 47.0528) | | | | | | | |
|---|---|---|---|---|---|---|---|
| Load (g) | 2400 (3 gmts) | Fabric: | Denim | Formula Time: | 1:30 | | |
| Machine: | 35# Milnor | Weight: | 14.5 oz | Developed by: | | | |

| Step | Operation | Time (min) | Level | Temp (F.) | Chemical | Amount | %OWG | pH |
|---|---|---|---|---|---|---|---|---|
| 1 | Desize | 10 | Med | 150 | Zeke | 48 g | 2 | |
| 2 | Drain Balance | | | | | | | |
| 3 | Rinse | 2 | Med | 140 | | | | |
| 4 | Drain Balance | | | | | | | |
| 5 | Rinse | 2 | Med | 130 | | | | |
| 6 | Drain Balance | | | | | | | |
| 7 | Abrasion | 75 | Low (15L) | 125 | MAP | 29 g | buffer | 6.7 |
| | | | | | DAP | 10 g | | |
| | | | | | C-1 | 1.2 g | 0.05 | |
| 8 | Drain Balance | | | | | | | |
| 9 | Wash | 10 | Ned | 160 | SSCE | 24 g | 1 | |
| 10 | Drain Balance | | | | | | | |
| 11 | Rinse | 3 | Med | 120 | | | | |
| 12 | Drain Balance | | | | | | | |
| 13 | Rinse | 3 | Med | 100 | | | | |
| 14 | Drain Balance | | | | | | | |
| 15 | Rinse | 3 | Med | 100 | | | | |
| 16 | Drain Balance | | | | | | | |
| 17 | Extract | 2 | | | | | | |

In the example above, and in commercial use, one skilled in the art will appreciate that the use of pumice stones in the stonewash process will enhance the overall stonewash effect on the garments.

The results in Table 14. show that the C1 cellulase preparations #47.0325 and #47.0528 performed better in terms of the overall level of abrasion achieved on the garments and well within the range of the bakstaining level of the other commercial neutral cellulase products tested.

TABLE 14

Comparison of C-1 Cellulase Preparations 47.0325 & 47.0528 To Commercial Neutral Cellulases Denimax XT & BTU 202-318 (which contains Denimax XT)

| | Cellulase | % OWG | Wt (g) | Detergent | T (° F.) | pH | t (min) |
|---|---|---|---|---|---|---|---|
| 1 | Denimax XT | 0.50 | 12.0 | no | 130 | 6.7 | 75 |
| 2 | C-1 47.0528 | 0.05 | 1.2 | no | 125 | 6.7 | 75 |
| 3 | C-1 47.0325 | 0.10 | 2.4 | no | 125 | 6.7 | 75 |
| 4 | Denimax XT | 0.50 | 12.0 | yes | 130 | 6.7 | 75 |
| 5 | C-1 47.0528 | 0.05 | 1.2 | yes | 125 | 6.7 | 75 |
| 6 | C-1 47.0325 | 0.10 | 2.4 | yes | 125 | 6.7 | 75 |
| 7 | BTU 202-318 | 2.50 | 60.0 | yes | 130 | SB | 75 |

TABLE 14-continued

Comparison of C-1 Cellulase Preparations 47.0325 & 47.0528 To Commercial Neutral Cellulases Denimax XT & BTU 202-318 (which contains Denimax XT)

| ABRASION (Most to Least) | BACKSTAINING (Least to Most) |
|---|---|
| Trial 5 | Trial 4 |
| Trial 6 | Trial 5 |
| Trial 2 | Trial 6 |
| Trial 3 | Trial 3 |
| Trial 4 | Trial 1 |
| Trial 1 | Trial 2 |
| Trial 7 | Trial 7 |

Legend for Table 14
All of the trials in Table 14 were cleaned up with Super Scour (nonionic detergent) at 1.0% OWG, 160 F. for 5 minutes.
SB = Self Buffered - the commercial product "ROCKSOFT" BTU 202-318 contains Denimax XT, detergent and a buffer system as well as other additives to help enhance the stone wash performance of this commercial product.

C. Tests with 60-L special washing machine. Whole denim garments were desized as described for the 2-L washing machine tests. Each wash test was made with 1 pair of jeans (700 g), 2.8 L liquid (fabric:liquid ratio 1:4). All jeans were from the same dye lot. They were prewashed using an oxidation method for 15 minutes, then dried. Blue jeans washed at neutral pH with formulated C1 cellulose preparations 47.0325 using 2.4 grams per trial and 47.0528 using 1.5 grams for one trial and using 1.0 gram for a second trial were compared directly against blue jeans washed under neutral pH conditions and similar formulations using Denimax XT at 12 grams per trial and two other commercial neutral cellulases; Bactosol JE using 2.0% OWG and BTU 202–318 using 2.0% OWG (Bactosol JE and BTU 202–318 contain Denimax XT, buffer, detergent as well as other additives to enhance their wash performance). Table 15. shows that the blue jeans from all three C-1 trials outperformed the three commercial neutral cellulase products in terms of the level of abrasion achieved as well as the overall color reduction of the garments. The level of backstaining on the blue jeans from all six trials was very good, they were very similar to one another and what one would expect and see when using Novo's neutral cellulase Denimax XT. The backstaining values for all three of these C-1 trials were within the range of the backstaining values as shown in Table 13. The finished garments from these trials and the trials as rated and shown in Table 14 above were rated in a blind study by four independent groups, of three or more people per group. The people that made up each of these groups are considered to be skilled in the art of stonewashing. They were asked to place each of the garments in the following order: (1) Greatest overall abrasion and color reduction to least overall abrasion and color reduction; and (2) Backstaining, lowest level of backstaining to highest level of backstaining (See Table 15).

TABLE 15

| TRIAL | ENZYME | DOSAGE | BUFFER | DETERGENT | ABRASION/COLOR REDUCTION | BACKSTAINING |
|---|---|---|---|---|---|---|
| Trial A | C-1 47.0528 | 1.5 grams | Phosphate | Yes | ++++++ | 5 |
| Trial B | C-1 47.0528 | 1.0 grams | Phosphate | Yes | +++++ | 2 |
| Trial C | C-1 47.0325 | 2.4 grams | Phosphate | Yes | +++++ | 4 |
| Trial D | Denimax XT | 12.0 grams | Phosphate | Yes | ++++ | 3 |
| Trial E | BTU 202-318 | 2.0% OWG | Phosphate | Yes | +++ | 6 |
| Trial F | Bactosol JE | 2.0% OWG | Citrate | Yes | +++ | 1 |

Legend for Table 15:
Abrasion/Color Reduction - ++++++ (+6) best (=>++++ (4) is considered good and was comparable to commercial netural cellulases (e.g. - Denimax XT)
Backstaining - The lower number the better (all jeans were judged to be within the range of backstaining as found when using Novo's Denimax TX). Neutral cellulase significantly decreased backstaining compared with traditional acid cellulases such as Trichoderma (see Example 13)
% OWG - % Of Weight of Garment, for example for 100 lbs of jeans dryweight at 1% OWG, 1 lb of enzyme is used.

D. Light reflectance. Another test to evaluate backstaining is to measure the light reflectance of a treated fabric. At the end of washing treatment, jeans samples were analyzed using a reflectometer at two different wavelengths: (1) the higher the signal detected at 680 nm (measured at the outside of the jeans), the lower the backstaining; and (2) the higher the signal detected at 420 nm (measured at the inside of the jeans), the lower the backstaining. Table 16. compares the reflectance values of denim jeans after treatment with commercial cellulases from Novo Nordisk and Genencor International to C-1 preparation #47.6.1.

TABLE 16

| Enzyme | 680 nm | 420 nm |
|---|---|---|
| Denimax L (neutral cellulase, Novo) | 23 | 20 |
| Primafast 100 (acid cellulase, Genencor) | 20 | 13 |
| C1 47.6.1 (neutral/alkaline cellulase) | 22 | 18 |

The light reflectance values for the C1 cellulase were similar to those obtained with Novo Nordisk's commercial product Denimax L, a neutral cellulase, at both 680 and 420 nm and the light reflectance values for C1 cellulase were significantly better than those obtained with Genecor's commercial product Primafast 100, a acid cellulase, at both 680 and 420 nm.

E. Tests in Semi-industrial Washing Machine.
Test #1.
2 Jeans, weight 1343 gr
Water ratio 6:1
pH 5.5
Temp. 54° C.
Enzyme: C1 (preparation #47.6.1) 12 gr (0.9%)
Abrasion time 90 minutes
Drop bath
Rinse 5 minutes with 1% non-ionic detergent at 66° C.
Drop bath
Rinse cold
Drop bath
Soften for 5 minutes with cationic softener at 49° C.
Extract and dry.
Test #2. The same procedure as Test #1, above, except Denimax 700 T (2% OWG 28.9 gr) enzyme was used and wash conditions were conducted at pH 7.0, 54° C.

C1 cellulase was compared to Denimax 700 T, a neutral cellulase commercial product made by Novo. All jeans were from the same dye lot. They were prewashed for 15 minutes using an oxidation method then dried.

The jeans treated with C1 cellulase preparation #47.6.1 showed slightly less abrasion and lower backstaining than the jeans treated with Denimax 700T cellulase.

EXAMPLE 10

C1 Cellulase as an Additive to Laundry Detergent

A. Soil Release from Cotton

Wash performance of C1 cellulase preparation #47.9.1 was tested using the wash-performance procedure PW 9406 (Solvay). Soil (ink) release from cotton fabric was tested by Delta Reflectance (%). Wash test compared a C1 cellulase preparation (#47.9.1) to Celluzyme 0.7 T from Novo Nordisk in the presence and absence of alkaline protease Opticlean L500. The results of this test are shown in the Table 17.

C1 cellulase has soil release properties from ink soiled cotton at neutral pH in a color type detergent as the cellulase enzyme from *Humicola insolens*.

TABLE 17

Detergent wash test with C1 cellulase(*)

| | CMC-ase dosage | Reflectance Data (%) | |
|---|---|---|---|
| Enzyme tested (pH 7.0) | (U/l) | 1 | 2 |
| Cellulzyme 0.7 T | 200 | 3.68 | 4.75 |
| Celluzyme 0.7 T | 500 | 2.68 | 4.07 |
| Celluzyme 0.7 T + 5000 DU/l (**) | 200 | 2.07 | 3.13 |
| Celluzyme 0.7 T + 5000 DU/l (**) | 500 | 2.08 | 3.22 |
| C1 # 47.9.1 | 200 | 2.18 | 2.88 |
| C1 # 47.9.1. | 500 | 2.77 | 3.72 |

TABLE 17-continued

Detergent wash test with C1 cellulase(*)

| Enzyme tested (pH 7.0) | CMC-ase dosage (U/I) | Reflectance Data (%) 1 | 2 |
|---|---|---|---|
| C1 # 47.9.1 + 5000 DU/l (**) | 200 | 1.15 | 1.91 |
| C1 # 47.9.1 + 5000 DU/l (**) | 500 | 2.81 | 3.30 |
| None (control) | none | 0 | 0 |

AADU = Du = Delft unit, Du/l = Defft unit per liter
(*) 40° C., 45 min, drying at 68° C., 75 min
(**) Alkaline protease Opticlean L500

B. Stability of C1 Cellulase to Serine Proteases

As serine proteases, a trypsin (3.2 μM, from Bovine Pancreas, activity 10,000–13,000 N-benzyl-L-argine ethylester (BAEE)/mg, Sigma T-8253) and an α-chymotrypsin (8 μM, from Bovine Pancreas, 40–60 U/mg, Sigma C-4129) were used.

The proteases were incubated with C1 cellulase at 20° C. and pH 7.0. Chymotrypsin did not decrease C1 activity for 12 hours and trypsin led to a slight decrease (around 20%) of C1 activity, see Table 18.

Trypsin and chymotrypsin did not significantly change the stability of C1 CMC-ase at pH-s 4.5 and 7.0 at 50° and 57° C., see Table 18.

TABLE 18

The effect of proteases on CMC-ase activity of C1 cellulase (# 47.9.1)

| Protease | Temperature (° C.) | pH | Incubation time (h) | CMC-ase activity remaining (%) |
|---|---|---|---|---|
| None (control) | 20 | 7.0 | 12 | 70 |
| +Chymotrypsin | 20 | 7.0 | 12 | 70 |
| +Trypsin | 20 | 7.0 | 12 | 50 |
| None (control) | 50 | 4.5 | 3 | 100 |
| +Chymotrypsin | 50 | 4.5 | 3 | 100 |
| +Trypsin | 50 | 4.5 | 3 | 100 |
| None (control) | 50 | 7.0 | 3 | 78 |
| +Chymotrypsin | 50 | 7.0 | 3 | 60 |
| +Trypsin | 50 | 7.0 | 3 | 68 |
| None (control) | 57 | 4.5 | 3 | 62 |
| +Chymotrtrypsin | 57 | 4.5 | 3 | 60 |
| +Trypsin | 57 | 4.5 | 3 | 62 |
| None (control) | 57 | 7.0 | 3 | 30 |
| +Chymotrypsin | 57 | 7.0 | 3 | 30 |
| +Trypsin | 57 | 7.0 | 3 | 30 |

C. The Effect of Citrate, EDTA, Tween-80 and Persulfate on CMC-ase activity

Changing from acetate to citrate buffer (a chelating agent) did not effect the of C1 CMC-ase activity (molarity of buffers—0.1 M, pH 4.5, 50 and 57° C.), see Table 19.

EDTA (Ethylene Diamine Tetraacetic Acid) (5 mM) as a chelating agent at pH 4.5 and 50° C. did not change CMC-ase activity. At pH 4.5 (57° C.) and at pH 7.0 (50° C.) EDTA caused slight decreases in CMC-ase activity. At pH 7.0 and 57° C., EDTA caused slight increase in CMC-ase activity, see Table 19.

Non-ionic detergent Tween-80 (3 g/L, polyoxyethylene sorbitane monooleate), did not change CMC-ase activity of C1 (at pH-s 4.5 and 7.0 and at 50 and 57° C., see Table 19.

Oxidizing agent persulfate (3 g/L) did not change CMC-ase activity of C1 (at pH-s 4.5 and 7.0 at 50 and 57° C.), see Table 19.

C1 CMC-ase is resistant to serine proteases (trypsin and chymotrypsin), chelating agents (EDTA, citrate), non-ionic detergent (Tween-80) and to oxidizing agent (persulfate).

TABLE 19

The effect of citrate, EDTA, Tween-80 and persulfate on activity of C1 cellulasese (# 47.9.1). Incubation time - 3 hours.

| Effector | Concentration | Temperature (° C.) | pH | CMC-ase activity remaining (%) |
|---|---|---|---|---|
| None (control) | — | 50 | 4.5 | 100 |
| Citrate | 0.1 M | 50 | 4.5 | 100 |
| EDTA | 5 mM | 50 | 4.5 | 100 |
| Tween-80 | 3 g/L | 50 | 4.5 | 100 |
| Persulfate | 3 g/L | 50 | 4.5 | 97 |
| None (control) | — | 57 | 4.5 | 62 |
| Citrate | 0.1 M | 57 | 4.5 | 65 |
| EDTA | 5 mM | 57 | 4.5 | 60 |
| Tween-80 | 3 g/L | 57 | 4.5 | 68 |
| Persulfate | 3 g/L | 57 | 4.5 | 65 |
| None (control) | — | 50 | 7.0 | 78 |
| EDTA | 5 mM | 50 | 7.0 | 50 |
| Tween -80 | 3 g/L | 50 | 7.0 | 52 |
| Persulfate | 3 g/L | 50 | 7.0 | 50 |
| None (control) | — | 57 | 7.0 | 30 |
| EDTA | 5 mM | 57 | 7.0 | 38 |
| Tween-80 | 3 g/L | 57 | 7.0 | 25 |
| Persulfate | 3 g/L | 57 | 7.0 | 30 |

EXAMPLE 11

Stone Wash Tests of Cellulase Samples Produced by Different Strains of Chrysosporium Preparations #-s 47.1000, 47.1001, 47.2000 and 47.2001 produced by different strains of Chrysosporium were used for wash test with 2-L special wash machine at pH 6.5, 50° C., during 60 min with 135 g of desized denim jean fabric. Total amount of CMC-ase activity per trial was constant and equal to 336 U/run. After drying abrasion and backstaining of garment was evaluated by Datacolor measurement. The results are presented in Table 20. The results show that cellulases produced from different strains of Chrysosporium demonstrate similar wash performance at neutral pH in terms of abrasion and backstaining levels to the cellulases produced by the C-1 species *Chrysosporium lucknowense* Garg 1966.

TABLE 20

Stone wash activity of cellulase preparations from different strains of Chrysosporium

| Preparation # | Abrasion (*) | Backstaining (**) |
|---|---|---|
| 47.1000 | 12.3 | 1.6 |
| 47.1001 | 12.1 | 1.6 |
| 47.2000 | 14.2 | 1.7 |
| 47.2001 | 14.6 | 1.6 |

(*) - reflectance from front side, the higher value the more abrasion, blank = 9.1
(**) - reflectance from back side, the higher value the more backstaining

EXAMPLE 12

Purification of Cellulase Components

1. Selection of the C1 samples for purification. The C1 cellulase preparation #47.11.1 was chose for further purification in view of the fact that 47.11.1 possessed (i) high protein content; (ii) high FPA and CMC-ase activity (see Table 4).

2. Isolation and purification of C1 complex component. The first purification step included ion exchange chromatography on DEAE-Spheron C-1000 (Chemapol, Czech Republic). Dry C1 cellulose preparation (1.5 g) was dissolved in 15 mL of 0.01 M Na-phosphate buffer, pH 7. The solution was centrifuged and the supernatant desalted using an Acrylex P-2 column. The desalted sample was then applied to the DEAE-Spheron column (2.5×40 cm) in 0.01 M phosphate buffer, pH 7. Flow rate was 1 mL/minute. Fraction I was eluted in the start buffer. Fraction II was eluted across a 0 to 1 M NaCl gradient. Fraction III was eluted in 1 M NaCl after the gradient was completed. All fractions possessed cellulolytic activities. Fraction III contained pigment because separation from pigment did not occur using DEAE-Spheron chromatography. Fractions I, II, and III were lyophilized to concentrate and preserve enzyme activity.

Fraction II was further purified by ion exchange chromatography on "MONO Q" "MONOBEADS" (Pharmacia Biotech, Uppsala, Sweden). "MONO Q" is a strong anion exchange resin which binds negatively charged molecules. 300 mg of Fraction II was dissolved in 3 mL of 0.01 M Na-phosphate buffer, pH 7, desalted, and applied on a "MONO Q" column (1.5×10 cm) in 0.01 M phosphate starting buffer. Fraction II-1 was eluted in start buffer, and Fraction II-2 was eluted across a 0 to 1 M NaCl gradient at a flow rate of 1 mL/minute. Both fractions showed cellulolytic activities. Fractions II-1 and II-2 were lyophilized.

3. SDS-PAGE of protein fractions. Gel electrophoresis was carried out in 10% separating polyacrylamide gel under denaturing conditions. Fraction I has two main protein bands (around 30 and 40 kDa), Fraction II-1 has 6–7 main bands (between 35–70 kDa), Fraction II-2 has three main bands (around 40, 50, and 60 kDa), Fraction III contains numerous bands and resembles the SDS-PAGE picture of the unfractionated C1 complex. Reagents and kits from Bio-Rad (USA) were used for SDS-PAGE plates (100×80×0.75 mm). Coomasee brilliant blue R-250 in 25% trichloracetic acid was used for protein staining.

4. pH-dependencies of CMC-ase activity of protein fractions. Table 21 represents the pH dependencies of CMC-ase activity of partially purified fractions of C1 cellulase. CMC-ase activity was measured at 50° C. (CMC was hydrolyzed for 10 minutes). To create the different pH ranges, the following buffer systems were used: acetate buffer (pH 4–5), phosphate buffer (pH 6–8), and carbonate buffer (pH 8.5–10). In addition, a universal buffer system was used which consisted of acetate, borate, and phosphate (pH 4–10).

TABLE 21

The effect of pH on CMC-ase activity of C1 protein fractions (50° C.).

| | CMC-ase activity (%) | | |
|---|---|---|---|
| pH | Fraction I | Fraction II-1 | Fraction III |
| 4.0 | 65 | 65 | 100 |
| 4.5 | 90 | 85 | 100 |
| 5.0 | 100 | 100 | 95 |
| 5.5 | 90 | 100 | 90 |
| 6.0 | 65 | 90 | 85 |
| 6.5 | 60 | 85 | 75 |
| 7.0 | 40 | 65 | 54 |
| 7.5 | 15 | 50 | 35 |
| 8.0 | 5 | 35 | 32 |

TABLE 21-continued

The effect of pH on CMC-ase activity of C1 protein fractions (50° C.).

| | CMC-ase activity (%) | | |
|---|---|---|---|
| pH | Fraction I | Fraction II-1 | Fraction III |
| 8.5 | 35 | 25 | 10 |
| 9.0 | 8 | 20 | 15 |

The pH-dependency of Fraction I after DEAE-Spheron had maxima under pH 5.0 and 8.5. Fraction II-1 (after DEAE-Spheron and "MONO Q" ion exchange chromatography) had a non-symmetric bell-type pH profile with a maximum at pH 5–6.5 and with a "shoulder" at pH 7–9 and a pH profile more or less the same as the pH profile of the unfractionated C1 preparation (see Tables 21. and Table 7.). Fraction III after DEAE-Spheron had a pH-optimum 4–5.5 with a "shoulder" at pH 6–9.

5. Stability of CMC-ase of protein Fraction I (after DEAE-Spheron). Table 22. shows temporal CMC-ase activity curves of Fraction I after DEAE-Spheron ion exchange chromatography at different pH (5.2–8.7) and 50° C. CMC-ase activity of Fraction I was most stable at pH 5.2–7.2 (around 35% to 45% of activity remained after 3 hours). At pH 7.7, 60% of activity was lost after about 1 hour, whereas at pH 8.3 and 8.7, 50% of activity was lost after about 0.5 hour. At pH 8.3, 100% of CMC-ase activity was lost after 3 hours, and at pH 8.7, 100% of activity was lost after 2 hours.

TABLE 22

Stability of CMC-ase of a protein fraction I after DEAE-Spheron at 50° C.

| | CMC-ase activity remained (%) | | | | |
|---|---|---|---|---|---|
| Time (h) | pH 5.2 | pH 7.2 | pH 7.7 | pH 8.3 | pH 8.7 |
| 0 | 100 | 100 | 100 | 100 | 100 |
| 0.5 | 97 | 75 | 65 | 50 | 50 |
| 1 | 90 | 55 | 40 | 25 | 15 |
| 2 | 40 | 50 | 35 | 10 | 0 |
| 3 | 30 | 45 | 25 | 0 | 0 |

EXAMPLE 13

C-1 Cellulase Production in 60 Liter Batch Fermentor

1. Inoculum Preparation

Inoculum preparations or starter cultures for the batch fermentation were prepared as follows. One milliliter (1 ml) of C-1 spore culture was used to inoculate each of two flasks to generate a total of 2.0 liters oculum. The starter culture was incubated at 150 rpm, at 30° C. for 56 hours.

| Medium for Inoculum Preparation* | |
|---|---|
| $K_2HPO_4$ | 0.5 g/L |
| $MgSO_4.7H_2O$ | 0.15 |
| KCl | 0.05 |
| $FeSO_4.7H_2O$ | 0.007 |
| yeast extract (ohly KAT) | 1.0 |
| peptone (Hormel PSR 5) | 10.0 |

-continued

| Medium for Inoculum Preparation* | |
|---|---|
| lactose | 10.0 |
| glucose | 10.0 |

*The pH -of the inoculum medium was adjusted to pH 7.0 with NaOH, the media was then autoclaved for 35 minutes at 121° C. in two six liter baffled flasks each containing one liter of medium.

2. Cellulase Production in 60 Liter Batch Fermenter (Preparation of 47.0325)

The two liter shaker flask inoculum culture prepared above, was used inoculate 40 liters of medium contained in a 60 liter fermenter. The medium for fermentation was as follows:

| Fermentation Medium* | |
|---|---|
| $K_2HPO_4$ | 0.22 g/L |
| $KH_2PO_4$ | 0.08 g/L |
| $(NH_4)_2SO_4$ | 4.0 g/L |
| $Na_3citrate.2H_2O$ | 4.0 g/L |
| $MgSO_4.7H_2O$ | 0.03 g/L |
| $CaCl_2.2H_2O$ | 0.4 g/L |
| $FeSO_4.7H_2O$ | 0.5 mg/L |
| $MnSO_4.7H_2O$ | 0.5 mg/L |
| $ZnSO_4.7H_2O$ | 0.2 mg/L |
| $CoCl_2.6H_2O$ | 0.24 mg/L |
| lactose | 5.0 g/L |
| yeast extract (ohly KAT) | 0.05 g/L |
| defatted cotton seed flour (Pharmamedia) | 5.0 g/L |
| cellulose (Signmacell 50) | 20.0 g/L |
| pH | 7.0 |

*The 40 liters medium was in deionized water, and was sterilized for 45 minutes at 121° C.

After inoculation of the fermentation medium, pH was maintained above 6.9 by addition of $NH_3$ and below 7.1 by addition of $H_2SO_4$. The fermenter was incubated for 64 hours with agitation and aeration as necessary to maintain dissolved oxygen greater than 30% of saturation.

3. Recovery of Cellulase Activity

Suspended solids from the fermented culture were removed by filtration on large Buchner funnel using Whatman 54 filter paper and 10 g/L Celite 503 as filter aid. The filtrate was collected, and the cellulase concentrated by ultrafiltration using 10,000 MW cutoff hollow fiber filter. The concentrate was freeze dried. The dried concentrate was designated cellulase preparation 47.0325. The activity of this preperation is given in Table 4.

EXAMPLE 14

Mutation Procedure Used to Generate Mutant Stain of C-1

A spore suspension was prepared using a Pridham agar plate (4 g/L yeast extract, 10 g/L malt extract, 10 g/L glucose, 15 g/L agar) containing a sporulated culture of strain C1. The plate was flooded with 10 ml of 0.05% Tween 80. The suspension was transferred to a sterile screw cap tube and vortexed on high for 1 minute. The suspension was then filtered through a column to remove mycelium. Spores were counted and diluted to $7 \times 10^5$ spores per ml in water. Ten mls of the spore suspension were transferred to a standard glass petri dish. The spores were irradiated for 75 seconds at 720 $\mu$Watts/cm$^2$ using a Pen-Ray UV bulb. The spore suspension was gently stirred throughout the irradiation using a sterile paper clip as a magnetic stir bar. Following irradiation, the spore suspension was taken to a foil wrapped tube, diluted in water and plated in dim light to $NH_4$ minimal medium as defined below. After incubating 20 days at 30 degrees C., a colony was identified as a large colony with a large zone of cellulose clearing around the colony.

$NH_4$ Minimal Medium, pH 7.5

1 g/L $K_2HPO4_4$
0.1 g/L KCl
0.3 g/L $MgSO_4.7H_2O$
0.1 g/L NaCl
16 mg/L $FeCl_3.6H_2O$
1.92 g/L$(NH_4)_2SO_4$
15 g/L Difco Noble agar
2.5 g/L acid swollen cellulose (added as a 1.25% stock after autoclaving)
0.5 g/L sodium deoxycholate (added after autoclaving)

EXAMPLE 15

C-1 Mutant Cellulase Production in 60 Liter Batch Fermentation Flasks (Preparation of 47.0528)

1. Inoculum Preparation

Preparations of starter cultures for the fed batch fermentation were prepared as described in Example 13 (section 1).

2. Cellulase Production In 60 Liter Batch Fermentation

The two liter inoculum was used to inoculate 40 liters of fermentation medium as described below.

| Fermentation Medium* | |
|---|---|
| $K_2HPO_4$ | 0.44 g/L |
| $KH_2PO_4$ | 0.16 g/L |
| $(NH_4).2SO_4$ | 3.0 g/L |
| $Na_2citrate.2H_2O$ | 4.0 g/L |
| $MgSO_4.7H_2O$ | 0.06 g/L |
| $CaCl_2.2H_2O$ | 0.8 g/L |
| $FeSO_4.7H_2O$ | 0.1 mg/L |
| $MnSO_4.7H_2O$ | 0.04 mg/L |
| $ZnSO_4.7H_2O$ | 0.04 mg/L |
| $CoSO_4.6H_2O$ | 0.048 mg/L |
| lactose | 5.0 g/L |
| yeast extract (ohly KAT) | 0.1 g/L |
| defatted cotton seed flour (Pharmamedia) | 10.0 g/L |
| cellulose (Sigmacell 50) | 20.0 g/L |

*The 40 liters medium was in deionized water, and sterilized by autoclaving for 45 minutes at 121° C.

3. Fermentation Conditions

The pH was maintained at around 7.0 and controlled by addition of $NH_3$ at pH above 6.9, and addition of $H_2SO_4$ at pH below 7.1. Incubation time was 87 hours, agitation and aeration were as necessary to maintain dissolved oxygen greater than 30% of saturation. At 40 hours, 3.0 liters of feed solution as described below, was added at a rate of 5.0 ml each 5 minutes.

| Feed Solution for Fermenter | |
|---|---|
| $K_2HPO_4$ | 0.88 g/L |
| $KH_2PO_4$ | 0.32 g/L |
| $(NH_4)_2SO_4$ | 4.0 g/L |
| $Na_2citrate.2H_2O$ | 4.0 g/L |
| $MgSO_4.7H_2O$ | 0.12 g/L |
| $CaCl_2.2H_2O$ | 0.16 g/L |
| $FeSO_4.7H_2O$ | 0.2 mg/L |
| $MnSO_4.7H_2O$ | 0.08 mg/L |
| $ZnSO_4.7H_2O$ | 0.08 mg/L |
| $CoCl_2.6H_2O$ | 0.096 mg/L |
| lactose | 20.0 g/L |
| yeast extract (ohly KAT) | 0.2 g/L |
| Pharmamedia | 20.0 g/L |
| cellulose (Sigmacell 50) | 20.0 g/L |

4. Recovery of Cellulase Activity

Suspended solids were removed by filtration on large Buchner funnel using Whatman 54 filter paper and 10 g/L Celite 503 as filter aid. The filtrate was collected and cellulase concentrated by ultrafiltration using 10,000 MW cutoff hollow fiber filter. The concentrate was dried by freeze-drying. The concentrate was designated cellulase preparation 47.0528 (activity is given in Table 4).

It should be understood that the examples and embodiments described herein are for illustrative purposes only and that various modifications or changes in light thereof will be suggested to persons skilled in the art and are to be included within the spirit and purview of this application and the scope of the appended claims.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A method of enzymatically treating cellulosic fibers or fabrics, comprising treating said fibers or fabrics with a neutral and/or alkaline cellulase whose amino acid sequence is encoded by a nucleic acid sequence from a fungus of the genus Chrysosporium, provided that, when said method is carried out at a pH below 7.0, said fungus is not *Chrysosporium pruinosum*.

2. A method of enzymatically treating cellulosic fibers or fabrics, comprising treating said fibers or fabrics with a neutral and/or alkaline cellulase isolated or obtained from a fungus of the genus Chrysosporium, provided that, when said method is carried out at a pH below 7.0, said fungus is not *Chrysosporium pruinosum*.

3. A method of stonewashing jeans, comprising treating said jeans with a neutral and/or alkaline cellulase whose amino acid sequence is encoded by a nucleic acid sequence from a fungus of the genus Chrysosporium, provided that, when said method is carried out at a pH below 7.0, said fungus is not *Chrysosporium pruinosum*.

4. The method of claim 3, wherein said Chrysosporium fungus is chosen from the group consisting of *Chrysosporium lucknowense, Chrysosporium pannorum, Chrysosporium pruinosum, Chrysosporium keratinophilum, Chrysosporium lobatum, Chrysosporium merdarium, Chrysosporium queenslandicum*, and *Chrysosporium tropicum*.

5. The method of claim 3, wherein said Chrysosporium fungus is *Chrysosporium lucknowense*.

6. The method of claim 5, wherein the fungus is *Chrysosporium lucknowense* Garg 27K, having accession number VKM F-3500D.

7. A method of stonewashing jeans, comprising treating said jeans with a neutral and/or alkaline cellulase isolated or obtained from a fungus of the genus Chrysosporium, provided that, when said method is carried out at a pH below 7.0, said fungus is not *Chrysosporium pruinosum*.

8. The method of claim 7, wherein said Chrysosporium fungus is chosen from the group consisting of *Chrysosporium lucknowense, Chrysosporium pannorum, Chrysosporium pruinosum, Chrysosporium keratinophilum, Chrysosporium lobatum, Chrysosporium merdarium, Chrysosporium queenslandicum*, and *Chrysosporium tropicum*.

9. The method of claim 8, wherein said Chrysosporium fungus is *Chrysosporium lucknowense*.

10. The method of claim 9, wherein the fungus is *Chrysosporium lucknowense* Garg 27K, having accession number VKM F-3500D.

11. A method of enhancing the softness or feel of cellulose- or cotton-containing fabrics, comprising treating said fabrics with a neutral and/or alkaline cellulase whose amino acid sequence is encoded by a nucleic acid sequence from a fungus of the genus Chrysosporium, provided that, when said method is carried out at a pH below 7.0, said fungus is not *Chrysosporium pruinosum*.

12. The method of claim 11, wherein said Chrysosporium fungus is chosen from the group consisting of *Chrysosporium lucknowense, Chrysosporium pannorum, Chrysosporium pruinosum, Chrysosporium keratinophilum, Chrysosporium lobatum, Chrysosporium merdarium, Chrysosporium queenslandicum*, and *Chrysosporium tropicum*.

13. The method of claim 12, wherein said Chrysosporium fungus is *Chrysosporium lucknowense*.

14. The method of claim 13, wherein the fungus is *Chrysosporium lucknowense* Garg 27K, having accession number VKM F-3500D.

15. A method of enhancing the softness or feel of cellulose- or cotton-containing fabrics, comprising treating said fabrics with a neutral and/or alkaline cellulase isolated or obtained from a fungus of the genus Chrysosporium, provided that, when said method is carried out at a pH below 7.0, said fungus is not *Chrysosporium pruinosum*.

16. The method of claim 15, wherein said Chrysosporium fungus is chosen from the group consisting of *Chrysosporium lucknowense, Chrysosporium pannorum, Chrysosporium pruinosum, Chrysosporium keratinophilum, Chrysosporium lobatum, Chrysosporium merdarium, Chrysosporium queenslandicum*, and *Chrysosporium tropicum*.

17. The method of claim 16, wherein said Chrysosporium fungus is *Chrysosporium lucknowense*.

18. The method of claim 17, wherein the fungus is *Chrysosporium lucknowense* Garg 27K, having accession number VKM F-3500D.

19. A method of enhancing the cleaning ability of a detergent composition, comprising adding to said detergent composition a neutral and/or alkaline cellulase whose amino acid sequence is encoded by a nucleic acid sequence from a fungus of the genus Chrysosporium, provided that, when said detergent composition has a a pH below 7.0, said fungus is not *Chrysosporium pruinosum*.

20. The methd of claim 19, wherein said Chrysosporium fungus is chosen from the group consisting of *Chrysosporium lucknowense, Chrysosporium pannorum, Chrysosporium pruinosum, Chrysosporium keratinophilum, Chrysosporium lobatum, Chrysosporium merdarium, Chrysosporium queenslandicum*, and *Chrysosporium tropicum*.

21. The method of claim 20, wherein said Chrysosporium fungus is *Chrysosporium lucknowense*.

22. The method of claim 21, wherein the fungus is *Chrysosporium lucknowense* Garg 27K, having accession number VKM F-3500D.

23. A method of enhancing the cleaning ability of a detergent composition, comprising adding to said detergent composition a neutral and/or alkaline cellulase isolated or obtained from a fungus of the genus Chrysosporium, provided that, when said detergent composition has a a pH below 7.0, said fungus is not *Chrysosporium pruinosum*.

24. The method of claim 23, wherein said Chrysosporium fungus is chosen from the group consisting of *Chrysosporium lucknowense, Chrysosporium pannorum, Chrysosporium pruinosum, Chrysosporium keratinophilum, Chrysosporium lobatum, Chrysosporium merdarium, Chrysosporium queenslandicum*, and *Chrysosporium tropicum*.

25. The method of claim 24, wherein said Chrysosporium fungus is *Chrysosporium lucknowense*.

26. The method of claim 25, wherein the fungus is *Chrysosporium lucknowense* Garg 27K, having accession number VKM F-3500D.

27. A method of biopolishing, defibrillating, bleaching, dying, or desizing textiles, comprising treating said textiles with a neutral and/or alkaline cellulase whose amino acid sequence is encoded by a nucleic acid sequence from a fungus of the genus Chrysosporium, provided that, when said method is carried out at a pH below 7.0, said fungus is not *Chrysosporium pruinosum*.

28. The method of claim 27, wherein said Chrysosporium fungus is chosen from the group consisting of *Chrysosporium lucknowense, Chrysosporium pannorum, Chrysosporium pruinosum, Chrysosporium keratinophilum, Chrysosporium lobatum, Chrysosporium merdarium, Chrysosporium queenslandicum*, and *Chrysosporium tropicum*.

29. The method of claim 28, wherein said Chrysosporium fungus is *Chrysosporium lucknowense*.

30. The method of claim 29, wherein the fungus is *Chrysosporium lucknowense* Garg 27K, having accession number VKM F-3500D.

31. A method of biopolishing, defibrillating, bleaching, dying, or desizing textiles, comprising treating said textiles with a neutral and/or alkaline cellulase isolated or obtained from a fungus of the genus Chrysosporium, provided that, when said method is carried out at a pH below 7.0, said fungus is not *Chrysosporium pruinosum*.

32. The method of claim 31, wherein said Chrysosporium fungus is chosen from the group consisting of *Chrysosporium lucknowense, Chrysosporium pannorum, Chrysosporium pruinosum, Chrysosporium keratinophilum, Chrysosporium lobatum, Chrysosporium merdarium, Chrysosporium queenslandicum*, and *Chrysosporium tropicum*.

33. The method of claim 32, wherein said Chrysosporium fungus is *Chrysosporium lucknowense*.

34. The method of claim 33, wherein the fungus is *Chrysosporium lucknowense* Garg 27K, having accession number VKM F-3500D.

35. A method of deinking or biobleaching paper or pulp, comprising treating said paper or pulp with a neutral and/or alkaline cellulase whose amino acid sequence is encoded by a nucleic acid sequence from a fungus of the genus Chrysosporium, provided that, when said method is carried out at a pH below 7.0, said fungus is not *Chrysosporium pruinosum*.

36. The method of claim 35, wherein said Chrysosporium fungus is chosen from the group consisting of *Chrysosporium lucknowense, Chrysosporium pannorum, Chrysosporium pruinosum, Chrysosporium keratinophilum, Chrysosporium lobatum, Chrysosporium merdarium, Chrysosporium queenslandicum*, and *Chrysosporium tropicum*.

37. The method of claim 36, wherein said Chrysosporium fungus is *Chrysosporium lucknowense*.

38. The method of claim 37, wherein the fungus is *Chrysosporium lucknowense* Garg 27K, having accession number VKM F-3500D.

39. A method of deinking or biobleaching paper or pulp, comprising treating said paper or pulp with a neutral and/or alkaline cellulase isolated or obtained from a fungus of the genus Chrysosporium, provided that, when said method is carried out at a pH below 7.0, said fungus is not *Chrysosporium pruinosum*.

40. The method of claim 39, wherein said Chrysosporium fungus is chosen from the group consisting of *Chrysosporium lucknowense, Chrysosporium pannorum, Chrysosporium pruinosum, Chrysosporium keratinophilum, Chrysosporium lobatum, Chrysosporium merdarium, Chrysosporium queenslandicum*, and *Chrysosporium tropicum*.

41. The method of claim 40, wherein said Chrysosporium fungus is *Chrysosporium lucknowense*.

42. The method of claim 41, wherein the fungus is *Chrysosporium lucknowense* Garg 27K, having accession number VKM F-3500D.

43. A method of restoring color to textiles, comprising treating said textiles with a neutral and/or alkaline cellulase whose amino acid sequence is encoded by a nucleic acid sequence from a fungus of the genus Chrysosporium, provided that, when said method is carried out at a pH below 7.0, said fungus is not *Chrysosporium pruinosum*.

44. The method of claim 43, wherein said Chrysosporium fungus is chosen from the group consisting of *Chrysosporium lucknowense, Chrysosporium pannorum, Chrysosporium pruinosum, Chrysosporium keratinophilum, Chrysosporium lobatum, Chrysosporium merdarium, Chrysosporium queenslandicum*, and *Chrysosporium tropicum*.

45. The method of claim 44, wherein said Chrysosporium fungus is *Chrysosporium lucknowense*.

46. The method of claim 45, wherein the fungus is *Chrysosporium lucknowense* Garg 27K, having accession number VKM F-3500D.

47. A method of restoring color to textiles, comprising treating said textiles with a neutral and/or alkaline cellulase isolated or obtained from a fungus of the genus Chrysosporium, provided that, when said method is carried out at a pH below 7.0, said fungus is not *Chrysosporium pruinosum*.

48. The method of claim 47, wherein said Chrysosporium fungus is chosen from the group consisting of *Chrysosporium lucknowense, Chrysosporium pannorum, Chrysosporium pruinosum, Chrysosporium keratinophilum, Chrysosporium lobatum, Chrysosporium merdarium, Chrysosporium queenslandicum*, and *Chrysosporium tropicum*.

49. The method of claim 48, wherein said Chrysosporium fungus is *Chrysosporium lucknowense*.

50. The method of claim 49, wherein the fungus is *Chrysosporium lucknowense* Garg 27K, having accession number VKM F-3500D.

* * * * *